US011446324B2

(12) United States Patent
Brown et al.

(10) Patent No.: US 11,446,324 B2
(45) Date of Patent: Sep. 20, 2022

(54) VETERINARY COMPOSITIONS FOR USE IN TREATING MASTITIS, AND ASSOCIATED METHODS

(71) Applicant: Zoetis Services LLC, Parsippany, NJ (US)

(72) Inventors: Christina Lee Brown, Kalamazoo, MI (US); Derek James Sheehan, Galesburg, MI (US); John Mark Heimlich, Portage, MI (US); Todd Foster, Kalamazoo, MI (US); Jeffrey Ellis Price, Middlebury, IN (US); Sumitra Rajagopalan, Montreal (CA); Alexandre Therrien, Montreal (CA); Oscar Suarez, Montreal (CA); Nicholas Finn Cunningham, Kalamazoo, MI (US)

(73) Assignee: Zoetis Services LLC, Parsippany, NJ (US)

( * ) Notice: Subject to any disclaimer, the term of this patent is extended or adjusted under 35 U.S.C. 154(b) by 0 days.

(21) Appl. No.: 15/956,849

(22) Filed: Apr. 19, 2018

(65) Prior Publication Data

US 2018/0303866 A1      Oct. 25, 2018

Related U.S. Application Data

(60) Provisional application No. 62/652,992, filed on Apr. 5, 2018, provisional application No. 62/487,601, filed on Apr. 20, 2017.

(51) Int. Cl.
| | | |
|---|---|---|
| *A61K 31/722* | (2006.01) |
| *A61K 9/00* | (2006.01) |
| *A61K 9/06* | (2006.01) |
| *A61K 31/545* | (2006.01) |
| *A61K 47/02* | (2006.01) |
| *A61K 47/12* | (2006.01) |
| *A61K 47/34* | (2017.01) |
| *A61K 47/38* | (2006.01) |
| *A61K 31/165* | (2006.01) |
| *A61K 47/36* | (2006.01) |
| *A61K 47/20* | (2006.01) |
| *A61K 31/43* | (2006.01) |
| *A61K 47/24* | (2006.01) |
| *A61K 47/10* | (2017.01) |

(52) U.S. Cl.
CPC .......... *A61K 31/722* (2013.01); *A61K 9/0024* (2013.01); *A61K 9/0041* (2013.01); *A61K 9/06* (2013.01); *A61K 31/165* (2013.01); *A61K 31/43* (2013.01); *A61K 31/545* (2013.01); *A61K 47/02* (2013.01); *A61K 47/10* (2013.01); *A61K 47/12* (2013.01); *A61K 47/20* (2013.01); *A61K 47/24* (2013.01); *A61K 47/34* (2013.01); *A61K 47/36* (2013.01); *A61K 47/38* (2013.01)

(58) Field of Classification Search
CPC ...... A61K 9/0012–0051; A61K 31/717; A61K 31/722; A61K 9/06; A61K 47/06; A61K 47/10; A61K 47/12; A61K 47/14; A61K 47/24; A61K 47/26; A61K 47/34; A61K 47/36; A61K 47/38; A61K 47/186; A61L 27/20–26; A61L 27/40–48; A61L 27/50–60

See application file for complete search history.

(56) References Cited

U.S. PATENT DOCUMENTS

| | | |
|---|---|---|
| 5,989,215 A | 11/1999 | Delmotte et al. |
| 6,254,881 B1 | 7/2001 | McNally et al. |
| 6,344,488 B1 | 2/2002 | Chenite et al. |
| 7,906,138 B2 | 3/2011 | Rankin |
| 8,226,969 B2 | 7/2012 | Williamson |
| 8,353,877 B2 | 1/2013 | Hallahan et al. |
| 9,034,348 B2 | 5/2015 | Ben-Shalom |

(Continued)

FOREIGN PATENT DOCUMENTS

| | | |
|---|---|---|
| EP | 0076068 A2 | 4/1983 |
| WO | WO 99/07416 A1 | 2/1999 |

(Continued)

OTHER PUBLICATIONS

Chiriac, A. et al "Sol gel method performed for biomedical . . . " Mini-Rev. Med. Chem., vol. 10, No. 11, pp. 1-24 (Year: 2010).*
Vudayagiri, S. et al "Methods to ease the release of thin polydimethylsiloxane . . . " Polym. Adv. Technol., vol. 25, pp. 249-257. (Year: 2014).*
Wang, T. et al "Preparation and properties of a novel thermo-sensitive hydrogel . . . " Int. J. Biol. Macromol., vol. 93, pp. 775-782. (Year: 2016).*

(Continued)

*Primary Examiner* — Leigh C Maier
(74) *Attorney, Agent, or Firm* — Womble Bond Dickinson (US) LLP

(57) ABSTRACT

The present disclosure relates generally to sol-gel polymer composites that comprise chitosan, a hydrophilic polymer, a polysiloxane, and a gelation agent in a suitable medium. Advantageously, the sol-gel polymer composite can form a durable seal or strong solid in response to one or more physiological stimulus. The disclosure further relates to medical and veterinary uses of the composite, particularly, methods and delivery systems for reducing or preventing the incidence of a mammary disorder in a dairy animal. More particularly, the disclosure includes methods and sol-gel polymer composite compositions for creating a physical barrier on the teat surface or in the teat canal or cistern of a non-human animal for prophylactic treatment of mammary disorders such as mastitis wherein the sol-gel polymer creates a seal in response to one or more physiological stimulus.

15 Claims, 9 Drawing Sheets

(56) References Cited

U.S. PATENT DOCUMENTS

| | | | |
|---|---|---|---|
| 2004/0197422 A1* | 10/2004 | Dorgan | A61K 9/0041 424/653 |
| 2005/0191270 A1* | 9/2005 | Gruening | A61K 9/0019 424/78.3 |
| 2010/0028434 A1 | 2/2010 | Chenite et al. | |
| 2010/0285113 A1 | 11/2010 | Shoichet et al. | |
| 2015/0080841 A1 | 3/2015 | Bradley et al. | |

FOREIGN PATENT DOCUMENTS

| | | | |
|---|---|---|---|
| WO | WO 2003/022245 A1 | 3/2003 | |
| WO | WO 2004/032899 A1 | 4/2004 | |
| WO | WO 2005/086641 A2 | 9/2005 | |
| WO | WO 2013/021186 A1 | 2/2013 | |
| WO | WO 2014/063735 A1 | 5/2014 | |
| WO | WO 2015/038281 A1 | 3/2015 | |
| WO | WO 2017/079216 A1 | 5/2017 | |
| WO | WO-2017156632 A1 * | 9/2017 | A61K 9/0024 |

OTHER PUBLICATIONS

Alvarez-Lorenzo, C. et al "Crosslinked ionic polysaccharides . . . " Adv. Drug Deliv. Rev., vol. 65, pp. 1148-1171. (Year: 2013).*

Truchetti, G. et al "Efficacy of extended intramammary ceftiofur therapy . . . " Can. J. Vet. Res., vol. 78, pp. 31-37. (Year: 2014).*

Liu, L. et al "In situ forming hydrogels based on chitosan . . . " Asian J. Pharm. Sci., vol. 11, pp. 673-683. (Year: 2016).*

Tang, Y. et al "Production and characterisation of novel injectable chitosan/methylcellulose . . . " Carbohyd. Polym., vol. 82, pp. 833-841. (Year: 2010).*

McConnell, E. et al "An investigation into the digestion of chitosan . . . " J. Pharm. Sci., vol. 97, No. 9, pp. 3820-3829. (Year: 2008).*

Brinker, C.J. et al, 1990, Sol-Gel Science: The Physics and Chemistry of Sol-Gel Processing, Academic Press, ISBN 0121349705.

Hench, L.L. et al., 1990, The Sol-Gel Process, Chemical Reviews, vol. 90, pp. 33-72.

PCT International Search Report and Written Opinion, PCT International Application No. PCT/US2018/028242, International filing date Apr. 19, 2018, dated Jun. 25, 2018.

* cited by examiner

VETERINARY COMPOSITIONS FOR USE IN TREATING MASTITIS, AND ASSOCIATED METHODS

CROSS REFERENCE TO RELATED APPLICATIONS

This application claims the benefit of U.S. Provisional Patent Application Nos. 62/487,601, filed Apr. 20, 2017, and 62/652,992, filed Apr. 5, 2018, both of which are expressly incorporated herein by reference in their entirety.

TECHNICAL FIELD

The present disclosure relates generally to unique sol-gel polymer composites and novel uses for them. More particularly, the disclosure relates to the sol-gel polymer composites that form a strong solid in response to a physiological stimulus, the strong solid having pre-determined permeability and mechanical properties in response to the physiological stimulus. The composites are easily injectable and have shear thinning properties making them useful in a wide range of human and animal health applications where it is desirable to inject a liquid that solidifies rapidly after injection in a subject. The disclosure also relates to new methods for protecting the mammary glands of dairy animals from pathogenic load by utilizing the composites as teat sealants to decrease or to prevent the incidence of mastitis in the animals.

BACKGROUND

The contents of all patents and publications cited in this specification are hereby incorporated by reference in their entirety.

Hydrogels are highly hydrated, macromolecular networks, dispersed in water or other biological fluids. Hydrogels that exhibit the specific property of increased viscosity with increased temperatures are known as thermoreversible, thermosensitive (or thermosetting) hydrogels. It is known that thermosensitive hydrogels may be prepared from polymers of natural origin such as chitosan, which is a commercially available, inexpensive polymer obtained by partial to substantial alkaline N-deacetylation of chitin, a linear polysaccharide, made of N-acetylglucosamine units, linked via β-1,4-glycosidic bonds. The deacetylation process is generally performed using hot, concentrated, hydroxide solutions, usually sodium hydroxide.

Chitosan is biocompatible, non-toxic, and non-immunogenic, allowing its use in the medical, pharmaceutical, cosmetic and tissue construction fields. For example, topical ocular applications and intraocular injections or transplantation in the vicinity of the retina have been used. Moreover, chitosan is metabolized-cleaved by certain specific enzymes, e.g., lysozyme, and can therefore be considered as biodegradable. In addition, it has been reported that chitosan acts as a penetration enhancer by opening epithelial tight junctions. Chitosan also promotes wound healing and exhibits antibacterial, antifungal and antitumor properties.

The complexity of biological structures such as natural tissue has resulted in researchers exploring the use of biomaterials and medical devices that are introduced on the skin or into the body of a subject as a liquid and that turn solid or solid-like through simple application or injection. For example, chitosan hydrogels have been shown to be useful for cartilage regeneration and prevention of knee pain associated with acute and chronic cartilage defects. Chitosan-based gels have also been shown to turn into and serve as scaffolds for the encapsulation of invertebral disc (IVD) cells by entrapping large quantities of newly synthesized anionic proteoglycan. Chitosan is known to form thermoreversible gels in the presence of several multivalent anions, such as phosphate derivatives. Temperature-controlled pH-dependent formation of ionic polysaccharide gels, such as chitosan/organo-phosphate aqueous systems, has been described, for example, in PCT International Publication No. WO 99/07416 and U.S. Pat. No. 6,344,488. However, hydrogels made from ionic polysaccharides such as chitosan are weak and usually form only after a relatively long waiting time, after mixing polymer and salt solution. This is mainly due to the fact that it is difficult to obtain homogenous, fully-hydrated chitosan solutions with a high concentration of chitosan, especially high molecular weight chitosan, due to its poor solubility. Further, several medical applications require provision of not only a simple sol-gel transition, but a solid structure with desired macroporosity and mechanical properties. Moreover, temperature is a non-specific stimulus and can be triggered by elements outside the human body such as hot weather or, for oral applications, simply drinking a hot beverage. Thus, there is a need for stimuli-responsive implants and patches that can reach desired mechanical and/or permeability properties only when triggered by specific physiological stimuli.

U.S. Pat. No. 9,034,348 discloses injectable chitosan mixtures forming hydrogels. There are described chitosan compositions which form a hydrogel at near physiological pH and 37° C., comprising at least one type of chitosan having a degree of acetylation in the range of from about 30% to about 60%, and at least one type of chitosan having a degree of deacetylation of at least about 70%. Further disclosed is a chitosan composition which forms a hydrogel at near physiological pH and 37° C. that includes at least one type of chitosan having a degree of deacetylation of at least about 70% and a molecular weight of from 10-4000 kDa, and at least one type of a chitosan having a molecular weight of from 200-20000 Da. Also disclosed are methods of preparation and uses of the chitosan compositions.

U.S. Patent Application Publication No. 2010/0028434 discloses temperature controlled and pH-dependent self-gelling biopolymeric aqueous solutions. There are described biopolymeric liquid aqueous compositions for producing self-gelling systems and gels, which comprises an acidic water-based medium, 0.1 to 10% by weight of a pH-gelling acid-soluble biopolymer, and 0.1 to 10% by weight of a water-soluble molecule having a basic character and a pKa between 6.0 and 8.4, or a water-soluble residue or sequence of the molecule having a basic character and a pKa between 6.0 and 8.4. The liquid compositions have a final pH ranging from 5.8 and 7.4, and form a stable solid and homogeneous gel within a temperature range from 10 to 70° C. Methods for preparing the compositions and uses thereof are also described.

U.S. Patent Application Publication No. 2010/0285113 discloses inverse thermal gelling composite hydrogels having enhanced stability. There are described composite hydrogels comprising a blend of an aqueous solution of an anionic polysaccharide or a derivative thereof, such as hyaluronan (also commonly referred to as hyaluronic acid) or a derivative thereof and an aqueous solution of methylcellulose or another water soluble cellulose derivative thereof, having dispersed polymeric particles, such as polymeric hydrophobic particles therein selected from microparticles and nanoparticles, and wherein the stability of the hydrogel is enhanced relative to the stability of the hydrogel alone. The polymeric particles may contain at least one therapeutic agent, in which case each therapeutic agent exhibits a linear sustained release rate that can be tuned or altered by selecting the appropriate polymer formulation of the microparticles and/or nanoparticles. The composite may be injectable, and in the absence of a therapeutic agent may be used as a bulking agent for reconstructive and cosmetic surgery or may act as a platform for subsequent delivery of therapeutic agents.

Insofar as veterinary health issues are concerned, mastitis is an inflammation of the mammary gland that is typically caused by bacteria which in most cases enter the gland via the teat orifice. During the non-lactating period or "dry period" in the gland, deposits of keratin in the teat orifice and the streak canal form a primary defense mechanism. A keratin plug that forms in the teat of the animal forms a protective barrier, and the immune-rich tissues of the Furstenburg's Rosette in the teat, as well as the natural protective factors of the dry-cow secretions, contain high levels of naturally occurring anti-bacterial substances (cationic proteins) which inhibit the passage of bacteria from the teat orifice to the teat cistern (papillary sinus) and gland cistern. However, this keratin plug and these natural immune defense mechanisms can be overcome by bacterial invasion as the animal enters into the dry period at the end of lactation, during the dry period of the animal, and/or during calving. As a result, bacteria invade the gland and cause mastitis during the dry period or, more particularly, immediately following calving.

The major pathogens causing mastitis are Staphylococcal species such as, for example, *Streptococcus agalactiae, Staphylococcus aureus* and the like, *Corynebacterium bovis, Mycoplasma,* coliforms such as, for example, Esherichia *coli, Klebsiella* spp., *Enterobacter* spp., and *Citrobacter* spp., environmental Streptococcal species such as, for example, Strep. *dysgalactiae,* Strep. *uberis,* and *Enterococcus* spp., *Pseudomonas* spp., etc. Although mastitis is mainly caused by bacteria, the inflammation can also be produced as a result of viral infection (e.g., bovine herpesvirus II and IV, a paravaccinia virus such as Pseudo Cowpox, and the like) or infection with atypical pathogens like mycotic (e.g., *Candida* spp. and *Aspergillus* spp.) or algal microbes (e.g., Prototheca spp.) with or without development of a secondary bacterial infection.

Mastitis due to the presence of pathogens can become a highly contagious condition within the confines of a dairy farm that results in huge production losses for the dairy industry.

Reduction of drinkable milk then occurs from the harmful pathogens' effects or various treatments that render the milk not fit for human consumption. While severe cases can end in death, unhindered outbreaks can also cause permanent damage to the animals' udders. As a major endemic disease of dairy animals, mastitis puts the animal welfare at risk and often entails rather costly veterinary care. The value of protecting the early lactation period from existing and new infections perpetuated from the dry period remains highly valuable to the industry. It is clear that the treatment and control of mastitis is an important goal to maintain the animal's health and to lower the high costs of milk production in the dairy industry.

To that end, products have been developed in an attempt to seal an animal's teat to prevent mastitis and other conditions, for example, barrier teat dips to seal the external surface and streak canal of the teat during periods of milking and internal teat sealants to block or to seal the teat canal or to plug the teat cistern during the dry period, especially for heifers and cows that have experienced one or more pregnancies previously.

Along with these products, several methods to reduce the incidence of mastitis are described in the art, for example, a method comprising sequentially delivering from a single delivery device an antimicrobial formulation and a seal formulation into the teat canal of a non-human animal wherein the seal formulation is nontoxic heavy metal salt such as bismuth (U.S. Pat. No. 8,353,877); a method of applying to the teat canal and/or teat sinus a composition comprising exogenous keratin (U.S. Pat. No. 8,226,969); a method of forming a physical barrier in the teat canal for prophylaxis during an animal's dry period by infusing an amount of a teat seal formulation into the teat canal of the animal, wherein the teat seal formulation comprises a bismuth-free, nontoxic, heavy metal salt of titanium, zinc, barium or combinations thereof and the physical barrier does not cause a black spot defect in dairy products made with milk from the animal (U.S. Pat. No. 7,906,138); a method of forming an anti-infective free physical barrier in the animal's teat canal for prophylactic treatment of mastitis during the dry period comprising the step of infusing a seal formulation into the teat canal of the animal without an anti-infective agent, wherein the seal formulation comprises a nontoxic heavy metal salt such as bismuth in a gel base of aluminum stearate with a vehicle such as liquid paraffin or a gel base comprising a polyethylene gel (U.S. Pat. No. 6,254,881) and the like.

However, none of the existing seal formulations or external dip products seals the teat of the dairy animal externally for a sufficient amount of time to prevent mastitis, particularly the form that can be fatal and/or very contagious in the animals, like among heifers. Moreover, while teat sealants have been established as a viable method to provide a higher level of protection regardless of antibiotic choice or administration, the current products on the market fail to meet the demand for ease of use and long-lasting tissue adherence, ease of removal, avoidance of milk contamination and prevention of black spot defect in aged cheese. What is needed, therefore, is a nontoxic formulation that is easy and safe for the animal handler to administer and that preferably forms an effective, long-lasting seal in place directly on the tissue (that is, "in situ"). Additionally, it is necessary for the seal formulation not to interfere with the quality of the dairy animal's milk, yogurt or cheese products created from the milk, especially for the sealant to avoid the black spot defect in aged cheese. Indeed, there is a definite art-recognized need in the veterinary field to find a long-lasting, nontoxic, non-irritating seal formulation that forms an adequate barrier on the animal's teat to prevent or to reduce significantly the incidence of mastitis caused by pathogens, preferably without the use of antibiotics or other medicinal agents that require a withholding period for public consumption of the animal's milk. There is also a definite need to find a long-lasting seal formulation that can contain antibiotics and the like for the effective treatment or prevention of mastitis.

It is an object of the present technology, therefore, to provide sol-gel polymer composites that ameliorate the inconveniences of the known hydrogels.

BRIEF SUMMARY

The present disclosure concerns new sol-gel polymer composites that comprise chitosan, a hydrophilic polymer, a polysiloxane, and a gelation agent in a suitable medium. Advantageously, the sol-gel polymer composite can form a durable seal or strong solid in response to one or more physiological stimulus. This disclosure further concerns a variety of medical and veterinary uses for the sol-gel polymer composites. Specifically, the disclosure involves new methods of forming a physical barrier in the teat canal of a dairy animal for the prophylactic treatment or prevention of mammary disorders that occur mainly as the animal enters the dry period or during the dry period, comprising the basic step of externally applying a sol-gel polymer composite to the teat of the animal or infusing the composite within the teat canal or cistern. Preferably, the composition gels or solidifies rapidly in response to one or more physiological stimulus to form a strong solid. This disclosure also provides systems for forming a physical barrier in the teat canal of a dairy animal for the treatment of mammary disorders, said system comprising a sol-gel polymer composite and an infusion device for infusing the composition into the teat cistern of the animal. Such systems permit the teat sealant to block the invasion of the mammary gland by a mastitis-causing microorganism or to decrease the occurrence or re-occurrence of infection.

BRIEF DESCRIPTION OF THE DRAWINGS

The background of the disclosure and its departure from the art will be further described herein below with reference to the accompanying drawings, wherein.

DETAILED DESCRIPTION OF THE DISCLOSURE

Figure 1A:
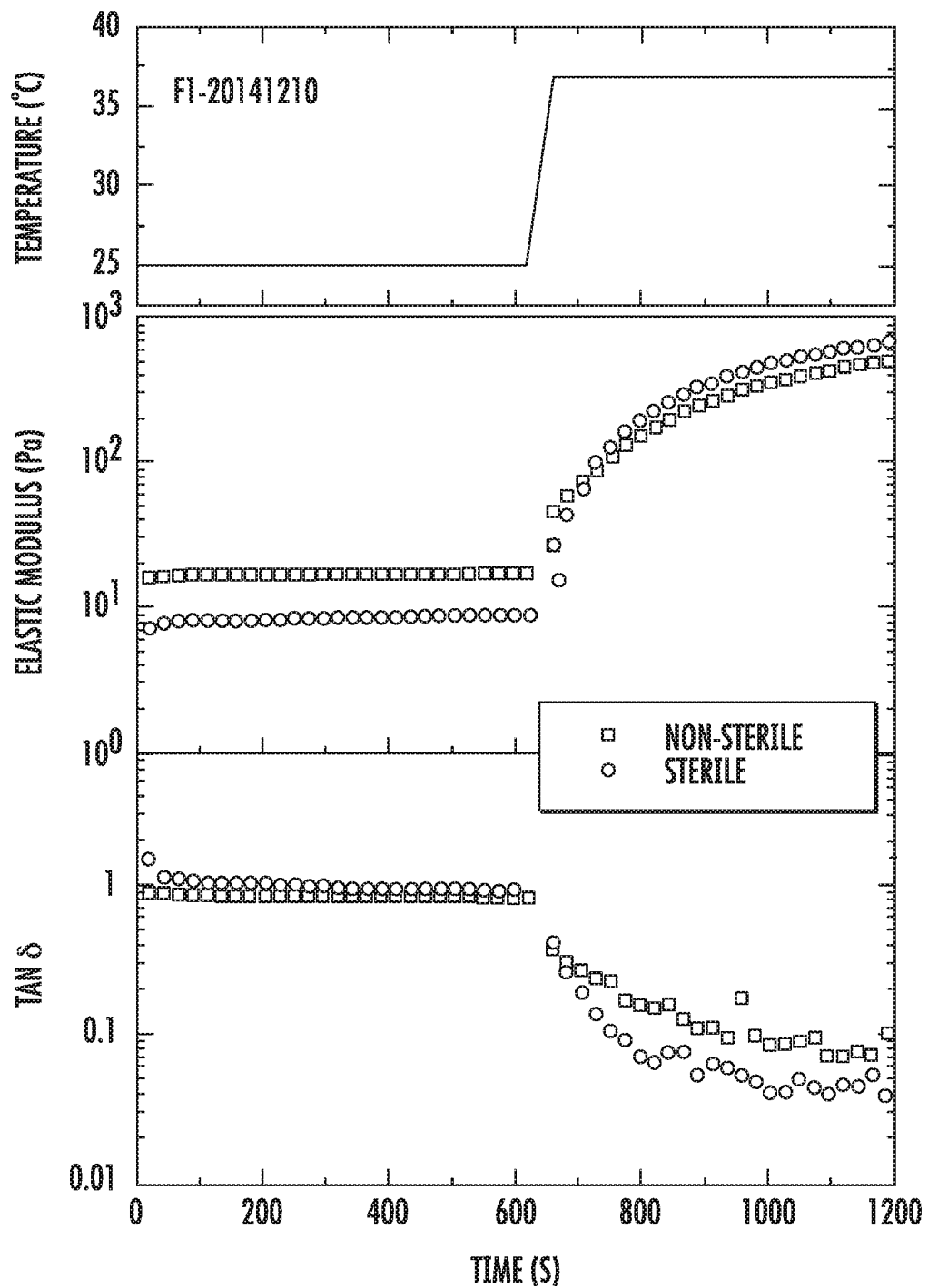
FIG. 1A shows graphs of time dependence of elastic modulus (G') and loss tangent (tan $\delta$=G"/G') upon a temperature jump from 25 to 37° C. recorded at f=0.1 Hz and oscillatory stress of $\tau$=1 Pa, for the F1-20141210 formulation.

In accordance with the present disclosure, there are provided novel sol-gel polymer composites which comprise chitosan, a hydrophilic polymer, and a gelation agent in a suitable medium, desirably an aqueous medium and more desirably, in a weakly acidic, aqueous-based medium. The sol-gel polymer composite has shear thinning properties such that the composite can be deformed in a syringe at room temperature. The sol-gel polymer composite is also capable of being injected using a single-barrel syringe and the like. Beneficially, the composite is capable of forming a solid, often an especially strong solid, in response to one or more physiological stimulus without the addition of any other agents. In the response to stimulus, the sol-gel polymer composite often solidifies rapidly. Another advantage is that the composite provides an instant-gelling strong solid capable of withstanding mechanical or hydraulic pressures in physiological conditions. Additionally, the composite is capable of forming a no-leak, no-drip plug after injection into a mammalian subject.

The disclosure further provides numerous medical and veterinary uses for the sol-gel polymer composites that benefit from the specially designed formulations. While human applications will become apparent from the disclosure, a preferred use relates to a unique method of forming a physical barrier in the teat canal of a dairy animal for the prophylactic treatment of mammary disorders that typically occur as the animal begins to dry off or during the dry period, comprising the step of administering a sol-gel polymer composite to the teat or within the teat canal of the animal, preferably embracing the composition that gels or solidifies rapidly in response to one or more physiological stimulus to form a durable seal or strong solid. Also, the disclosure provides new methods of treatment that block the invasion of the mammary gland by mastitis-causing microorganisms and reduce or prevent the incidence of new infections or re-infection.

This disclosure includes systems for forming a physical barrier, which is preferably an internal barrier within the teat canal, of a dairy animal to prevent mammary disorders or to lessen the harmful effects of infection, said system comprising a sol-gel polymer composite and a delivery device for infusing the composition into the teat cistern of the animal. Such systems permit the treatment to block the invasion of the mammary gland by a mastitis-causing microorganism or to decrease the risk of the occurrence or re-occurrence of infection. More particularly, the present disclosure provides methods and systems wherein the sol-gel polymer composite is infused predominantly as the animal begins to dry off or during the dry period of a dairy livestock animal, preferably a heifer or a cow, but also can include other animals such as goats, sheep, water buffaloes and the like. The sol-gel polymer composite acts as an aid in the prevention and the control of mastitis during the dry off period, thus reducing the clinical and sub-clinical cases during the dry off period and in the first stage (post calving) of lactation. By remaining in the teat canal throughout the dry period, the sol-gel polymer composite eliminates or reduces microbial invasion through the teat canal during high risk periods in the pre-fresh dairy animal.

In one aspect, the disclosure provides methods for combatting microbial mammary mastitis in a dairy animal which method permits milk obtained from the animal to be used in the production of a milk product, the method comprising applying topically or infusing a sol-gel polymer composite directly on the relevant mammary tissue of a dairy animal or within the teat canal to form a teat seal. This teat sealant would typically be administered via intramammary administration to each teat at the time of drying-off. Preferably, the sol-gel polymer composite is applied or infused prior to infection of a healthy animal. In another aspect, the disclosure provides methods for reducing the withholding time of milk obtained from an animal being treated for mastitis before public consumption is allowed in the production of a milk product, wherein the sol-gel polymer composite is applied topically to or infused within the teat canal of the animal. The present disclosure also provides methods for reducing the withholding time of milk obtained from an animal being prophylactically treated to prevent or to reduce the frequency of mastitis in order to improve the production of a milk product, wherein a sol-gel polymer composite is applied topically to or infused within the teat canal of the animal.

Even more particularly, the present disclosure provides the above methods wherein the dairy product is milk, yogurt or cheese. When the dairy product is milk, the methods encompass dry or fluid milk. Also, the disclosure provides such methods wherein the sol-gel polymer composite is administered via intramammary infusion or by dipping the teat. In all embodiments, the non-human animal in need of the relevant veterinary uses of the present disclosure is preferably a heifer or cow but also can be another dairy livestock animal; and the administration is preferentially achieved by intramammary infusion as the animal begins to dry off or during the dry period. Moreover, the disclosure provides such methods wherein the sol-gel polymer composite is administered during the postpartum period of a non-lactating animal or wherein the sol-gel polymer composite is administered during the prepartum period of an animal.

The teat sealant of the present disclosure provides many advantages over the current sealants on the market through enhanced ease of use (both administration and removal) as well as in the total sum of its novel quality profile, for instance, the sol-gel polymer composite's nontoxicity, biocompatibility, biodegradability, elasticity (pliability), long-lasting tissue adherence, syringability, fluidity at room temperature, ability to solidify in response to body temperature, fast gelation time at 37° C., nonirritating and inert nature, etc. Notably, the infusible aqueous-based, thermal-transition sol-gel hydrogels are uniquely fluid at room temperature yet form a gel at body temperature in the teat canal. The sol-gel polymer formulations demonstrate a tailorable shear thinning characteristic which allows for ease of infusion over a wide temperature range as well as removal by manual stripping from the teat canal. Upon removal from the body cavity, the sol-gel polymer composite returns to a liquid phase at room temperature which supplies a real benefit to the dairies. In addition, unlike current commercial sealants, the teat sealant of this disclosure does not stick to the stainless steel pipes (milk lines) or bulk tanks during the initial processing stage of milk and is cleanable (that is, will readily clean off the industrial surfaces) during standard cold or hot water washes, which ultimately avoids milk contamination thereby preventing the black spot defect often seen in aged cheese and caused by known, conventional teat sealants.

Also beneficially, the teat sealant of the disclosure eliminates or significantly reduces the withholding time of milk obtained from a non-human animal being treated prophylactically for mastitis thereby avoiding or decreasing the standard milk discard period that is required when the animals are given antibiotics. Equally practical, the teat sealant can be preferentially designed to be fully compatible with cheese starter cultures when prepared with a relatively neutral pH by varying the salt component of the sol-gel polymer composite. Colostrum from treated animals is also safe to feed to calves.

Definitions

It should be appreciated that all scientific and technological terms used herein have the same meaning as commonly understood by those of ordinary skill in the art. The following definitions are given merely to illustrate the general meanings of the main terms used in connection with the present disclosure.

The term "udder" refers herein to the glandular, mammary structure of a female ruminant animal such as a cow, a goat, a sheep, a water buffalo and the like. In the cow, it comprises four independent glands, with one teat and one exit duct each, whereas sheep and goat have two glands. The term "teat" refers herein to the projecting part of the mammary gland containing part of the milk or teat sinus.

The term "teat sealant" refers herein to compositions and devices used to form a physical barrier on the surface of or inside an animal teat. A teat sealant can be on the teat surface, inside the teat streak canal, and/or inside the teat cistern.

The term "antimicrobial" refers herein to a substance that kills or inhibits the growth or reproduction of microorganisms such as bacteria, viruses, fungi, yeast, or protozoans.

The term "solution" refers herein to solutions, suspensions, or dispersions, unless otherwise stated. The term "spray" as used herein refers to an atomized composition, such as comprised of small or large liquid droplets, such as applied through an aerosol applicator or pump spray applicator for the intended purpose of delivering a broad application of the composition.

The term "stream" refers herein to a continuous, direct, and focused application of the composition. The term "infusion" refers herein to the continuous introduction of a fluid or solution into a cavity, vein or cistern.

The term "mammal" refers herein to a warm-blooded vertebrate animal of the class Mammalia, which includes both human and animal, that possess hair or fur on the skin, the secretion of milk from milk-producing mammary glands by females for nourishing the young, and a four-chambered heart.

For the embodiments of the disclosure that relate to mastitis, the term "animal" refers herein to a female, non-human mammal which has a lactation period, which includes, but is not limited to, livestock animals, such as cows, sheep, goats, horses, pigs, water buffaloes and the like. Preferably, the animal is a dairy cow. While both the "cow" and the "heifer" are female bovines, the term "heifer" refers herein to any young female cow that has not given birth to a calf, typically one that has been weaned and under the age of 3 years. The term "cow" often refers to an older female animal that has given birth to a calf.

The term "dry period" refers herein to the non-lactating phase of the lactation cycle of a cow or other dairy animal. It occurs between the end of one lactation cycle and the beginning of the next lactation. At the end of each lactation cycle, the animal begins the phase of "drying off" as the animal enters the dry period which includes the usual physiological, metabolic and endocrine changes associated with cessation of milk production for the non-lactating period (dry period) of the animal.

The term "milk product" refers herein to a product containing any amount of milk in liquid or powder form. It also includes cheese and yogurt.

The term "postpartum" refers herein to the period of time beginning immediately after calving and extending for about six weeks. The term "prepartum" refers herein to the period of time during pregnancy, which is prior to calving. The term "periparturient" refers herein to the period immediately before and after calving.

The term "involution" refers herein to the first two to three weeks after cessation of milk production in a cow.

The term "keratin plug" refers herein to keratin-based occlusion of the teat canal/streak canal of a cow following cessation of milk production for the dry period.

The term "microbial invasion" refers herein to movement of pathogenic microorganisms such as, for example, bacteria, especially pus-forming or necrotizing bacteria, viruses, fungi, yeast, protozoans and the like that proliferate into bodily tissue or bodily cavities, resulting in tissue injury that can progress to infection and/or disease. For purposes of the disclosure, the "microbial invasion" typically refers herein to a "bacterial invasion."

The term "sol-gel polymer composite" refers herein to a polymer composition that can undergo a sol-gel process to form a sol-gel state under certain conditions, as described herein. The terms "solid" and "gel," and "solidification" and "gelation" are used interchangeable herein to refer to the gel/solid formed after the sol-gel phase transition has occurred in response to one or more physiological stimulus.

The term "polymer" refers herein to a material that includes a set of macromolecules. Macromolecules included in a polymer can be the same or can be differ from one another in some fashion. A macromolecule can have any of a variety of skeletal structures, and can include one or more types of monomeric units. In particular, a macromolecule can have a skeletal structure that is linear or non-linear. Examples of non-linear skeletal structures include branched skeletal structures, such those that are star-branched, comb-branched, or dendritic-branched, and network skeletal structures. A macromolecule included in a homopolymer typically includes one type of monomeric unit, while a macromolecule included in a copolymer typically includes two or more types of monomeric units. Examples of copolymers include statistical copolymers, random copolymers, alternating copolymers, periodic copolymers, block copolymers, radial copolymers, and graft copolymers.

As used herein with reference to a polymer, the term "molecular weight (MW)" refers to a number average molecular weight, a weight average molecular weight, or a melt index of the polymer.

The term "elastic modulus" (also referred to as "Young's modulus" or the storage modulus (G')) is defined herein as the change in stress with an applied strain (that is, the ratio of shear stress (force per unit area) to the shear strain (proportional deformation)) in a material. Essentially, the elastic modulus is a quantitative measurement of stiffness of an elastic material that measures the ability of the tested material to return to its original shape and size. G' can be calculated using a formula derived from Hooke's law, which states that the elastic modulus is equal to the ratio of stress to strain (i.e., the ratio of applied pressure to fractional change in size).

The measure of the elastic modulus is reported as the force per unit area (the standard metric ratio of the Newton to unit area ($N/m^2$) or the pascal (Pa) in which one pascal is equivalent to one Newton (1 N) of force applied over an area of one meter squared (1 $m^2$)). This pascal unit is an art-recognized term often used to define a unit of pressure, tensile strength, stress and elasticity.

The term "shear thinning" as used herein refers to the common characteristic of non-Newtonian fluids in which the fluid viscosity decreases with increasing shear rate or stress. Shear thinning is observed in suspensions, emulsions, polymer solutions and gels. Due to shear thinning attributes, decreasing the viscosity of a polymer, a macromolecule or gel is made possible by increasing the rate of shear. Basically, as a result of the decrease in viscosity upon increase in shear rate, the "shear thinning" property is a measure of the ability of the hydrogel network to be temporarily deformed through the application of a gentle manual pressure from the piston of a syringe. This shear thinning phenomenon may be used, for instance, to make an otherwise stiff biocompatible hydrogel infusible.

The term "loss tangent tan δ" or "tan δ" refers herein to the tangent of the phase angle, that is, the ratio of viscous modulus (G") to elastic modulus (G') and a helpful quantifier of the presence and the degree of elasticity in a fluid. The tan δ values of less than unity indicate elastic-dominant (i.e. solid-like) behavior and values greater than unity indicate viscous-dominant (i.e. liquid-like) behavior. In an elastic solid, tan δ"=0.

As used herein, "strong" is intended to mean the elastic modulus G' that can generally range widely from about 420 Pa or higher, about 600 Pa to about 10,000 Pa, or about 6000 Pa to about 10,000 Pa, etc. at physiological temperature. Based on the level of stiffness, a solid body, for example, deforms when a load is applied to it. If the material is elastic, the body returns to its original shape after the load is removed. A "strong solid" is generally a gel or solid formed after the sol-gel phase transition for which G' at physiological conditions (e.g., 37° C., and/or near physiological pH) is typically above about 560 Pa, although strong solids may form below about 560 Pa or above about 10,000 Pa depending on other factors in the processing steps to make, to sterilize or to store the formulation.

The term "physiological temperature" used herein is intended to mean the normal body temperature range for a mammal, e.g., about 35° C. to about 40° C., about 36° C. to about 40° C., about 37° C., about 37.5° C. and the like.

The term "one or more physiological stimulus" refers herein to a selection of one or more stimulus embracing, but not limited to, temperature (e.g., body temperature such as a temperature from about 36° C. to about 40° C., or about 37° C.), pH (e.g., near physiological pH, alkaline or acidic conditions), ionic strength (e.g., hypotonic or hypertonic conditions) and the like. Other types of physiological stimuli include exposure to a bodily fluid such as, for example, breast milk or other secretions, blood, and the like. Another type of stimuli may arise from contact with a bodily chemical or macromolecule such as without limitation ions, electrolytes, calcium, sodium, cytotoxins, macrophages, enzymes, antigens, glucose, estrogen, etc.

Components and Characteristics of the Composition

In general, the sol-gel polymer composite of the present disclosure comprises chitosan, a hydrophilic polymer, a polysiloxane, and a gelation agent in a suitable acidic water-based medium. Optionally, the sol-gel polymer composites further include an emulsifier, a reinforcing agent such as suitable nanocrystalline fillers, a solid particulate or a water-soluble additive, and/or one or more antimicrobial agents. Advantageously, the sol-gel polymer composite forms a durable seal or a strong solid in response to one or more physiological stimulus. The formulations exhibit a unique combination of deliverability, swelling, and adhesion.

For the elements of the new sol-gel polymer composite, the chitosan is acylated in some instances, for example, the chitosan comprises acyl chitosan which includes, but is not limited to, carboxymethyl chitosan (CMCh). In some embodiments, the chitosan has a degree of deacetylation (% DDA) of at least about 75%, at least about 77%, at least about 80%, or at least about 90%. In some embodiments, the chitosan has a % DDA of about 75%, about 77%, about 80%, about 95%, about 96%, about 97%, about 98%, about 99%, or higher. The hydrophilic polymer includes, but is not limited to, methyl cellulose (MC) such as methyl cellulose ethers or cellulose ethers, polyvinyl acetate (PVA), PVA-acylate, hydroxypropyl cellulose (HPC), ethyl hydroxyethyl cellulose (EHEC), hydroxypropyl methylcellulose (HPMC), hypromellose acetate succinate (HPMC-AS), hyaluronic acid (HA), a poloxamer (a nonionic triblock copolymer) such as Pluronic® (e.g., Pluronic® F127 and P123), polyethylene glycol (PEG), gelatin, sodium alginate, or another water-soluble polysaccharide capable of forming a highly viscous thermosensitive gel. The hydrophilic polymer may be acylated. Desirably, the sol-gel polymer composite comprises methyl cellulose or PVA-acylate, which forms a thin mixture (slurry) after dissolution in cold water and a thick gel at physiological temperatures.

Usually, the gelation agent is a thermogelling element that undergoes physical crosslinking in response to a stimulus, e.g., temperature. In some embodiments, the gelation agent is a salt, such as, β-Glycerophosphate disodium hydrate or pentahydrate, sodium pyrophosphate tetrabasic, potassium phosphate dibasic trihydrate, sodium hexametaphosphate, sodium tetrapolyphosphate, sodium hexapolyphosphate, sodium heptapolyphosphate, sodium octapolyphosphate, sodium tripolyphosphate, sodium polyphosphate, potassium ferricyanide, mixtures thereof and the like. Advantageously, the gelation agent is a mixture of sodium pyrophosphate tetrabasic and potassium phosphate dibasic trihydrate salts. According to some aspects, the gelation agent is an ionic crosslinking agent selected from the group consisting of lipophilic phosphates (including octyl- and octadecyl-phosphonic acid salts), plasticizers (including acetyl tributyl citrate), anionic surfactants (octyl sulfate, lauryl sulfate, hexadecyl sulfate, cetylstearyl sulfate), gums (including xanthan gum), pectin, carrageenan (iota, kappa, and lambda), alginate, cyclodextrins, and a mixture thereof. According to some aspects, the gelation agent is a chemical crosslinking agent such as genipin, diethylsquarate, disuccinimidyl suberate, glutaraldehyde, dicarboxylic acid (including suberic acid, glutamic acid, succinic acid), diisocyanate, a mixture thereof and the like. The terms "gelation agent" and "gelator" are used interchangeably herein.

Using chitosan solution (pH<6), gel formation occurs with a number of different multivalent anionic counter ions. By mixing chitosan solution (pH<6) with anionic crosslinking solutions (pH>6), a true ionotropic gel may be formed. The $NH_2$ groups of chitosan are protonate and an ionic crosslinking occurs.

Chitosan cross-linked with high molecular weight counterions results in capsules, while cross-linking with low molecular weight counterions results in globules. Examples of high molecular weight counterions include, but are not limited to, poly(l-hydroxy-1-sulfonate-2-propene), poly(aldehydocarbonic acid), xanthane, pectin and the like. Examples of low molecular weight counterions include, but are not limited to, pyrophosphate, tripolyphosphate, tetrapolyphosphate, octapolyphosphate, hexametaphosphate, ferricyanide, hexacyanoferrate (III), potassium ferricyanide and the like. Using more hydrophobic counterions, hydrophobic systems may be prepared. Examples of such hydrophobic counterions include, but are not limited to, octyl sulfate, lauryl sulfate, hexadecyl sulfate, cetylstearyl sulfate and the like.

The polyphosphates represented can be linear or cyclic and can be coupled to H O or Na O. Specific examples of a polyphosphate that can be employed with the present invention can include sodium hexametaphosphate, sodium tetrapolyphosphate, sodium tripolyphosphate, sodium hexapolyphosphate, sodium heptapolyphosphate, sodium octapolyphosphate and the like.

It is preferable to prepare the sol-gel polymer composites in a weakly acidic aqueous-based medium such as, for example, 0.1 M aqueous acetic acid.

The formulation of the sol-gel polymer composites may optionally encompass a density modifier such as calcium carbonate or aluminum oxide. The material may be added into the sol-gel polymer composite to increase the specific gravity of the composition. Examples include, but are not limited to, calcium chloride, calcium carbonate, calcium sulfate, titanium oxide, silicon dioxide, chromium sulfate, chromium chloride, zinc oxide, iron sulfate, a mixture thereof and the like.

The formulation of the sol-gel polymer composites may optionally encompass a reinforcing agent such as a nanocrystalline filler. The strengthening material referred to as the "nanocrystalline filler" is generally a nanocrystalline material, e.g., a nanocrystalline particle or polymer, capable of providing mechanical reinforcement to the sol-gel polymer composite through noncovalent physical interactions such as, without limitation, hydrogen bonds or electrostatic attractions. Examples include, but are not limited to, nanocrystalline cellulose (NCC), an inorganic clay, an organic clay, carbon black, fumed silica, graphene, graphite and the like. Preferably, the nanocrystalline filler is nanocrystalline cellulose (NCC). Alternatively, the nanocrystalline filler comprises, for instance, a nanocrystalline starch, nanoclay, graphene, a carbon nanotube, organic nanoclay, or an organoclay. For another example, the nanocrystalline filler may be montmorillonite, bentonite, kaolinite, hectorite, halloysite, etc.

In some embodiments, the sol-gel polymer composites comprise a reinforcing agent such as an inorganic filler, e.g., silicon dioxide ($SiO_2$), titanium oxide ($TiO_2$).

In some embodiments, the sol-gel polymer composites further comprise calcium phosphate as the reinforcing agent. In other embodiments, the sol-gel polymer composites form a double network hydrogel for reinforcement of a strong solid phase. Double network gels are characterized by a special network structure consisting of two types of polymer components and have both a high water content (about 90% w/w) and high mechanical strength and toughness.

The formulation of the sol-gel polymer composites may encompass a solid particulate additive, a water-soluble additive, or a polymeric additive to improve mechanical properties. These additives are capable of providing mechanical reinforcement to the sol-gel polymer composite through noncovalent physical interactions such as, without limitation, hydrogen bonds or electrostatic attractions. Examples include, but are not limited to, water soluble poly(ethylene oxide), polyacrylic acid, Carbopol® cross-linked polyacrylic acid polymers, polyvinlypyrrolidone, poly(vinyl alcohol), fatty acids (including stearic acid), emulsifiers (including glycerol monostearate, glycerol monolaurate), polyacrylamide, bisacrylamide, Aerosil® R 972 hydrophobic silicon dioxide, polysiloxanes such as dimethylpolysiloxane (PDMS), etc.

The polysiloxane may be a silicone material, which in some instances includes a filler. According to one aspect, the polysiloxane may be ELASTOSIL® available from Wacker Chemie AG. The polysiloxane may be provided as a hydrophobic additive used for cohesiveness and stability of the formed plug. In some instances ELASTOSIL® RT 625 A may be used, which includes polydimethyl hydrogenmethyl siloxane, silazane treated silica—HDK, and polydimethylsiloxane vinyl terminated, in proprietary amounts.

Compositions in accordance with the present disclosure may include a polysiloxane present in the amount of about 70% or less by weight of the composition, and preferably present in the amount from about 5% to about 70% by weight of the composition, and more preferably present in the amount form about 30% to about 70% by weight of the composition, and more preferably in the amount of about 45% to about 55% by weight of the composition, and even more preferably in the amount of about 50% to about 51% by weight of the composition. Such compositions including a polysiloxane may further include a salt solution (including salt mixtures) in the amount of about 0.25% to about 0.35% by weight of the composition, chitosan in the amount of about 0.5% to about 1.5%, and more particularly about 1%, by weight of the composition, acetic acid in the amount of about 0.4% to about 0.6%, and more particularly about 0.5%, by weight of the composition and a hydrophilic polymer (e.g., methylcellulose) in the amount of about 4.5% to about 5.5% by weight of the composition. In some instances, a first and second salt component may be provided.

Such compositions having polysiloxane may have the following physical properties: a maximum initial (pre-shear) viscosity range of about 400-1400 Pa-s; average sheared viscosity range of about 10-25 Pa-s; structure recovery range of about 96%-250%; specific gravity (density) in the range of about 1.03-1.1 g/mL; syringe force of about 130-150 N; and a pH in the range of about 4.0-6.2.

The composition may also optionally include one or more pharmaceutical agents, particularly antimicrobial agents having antibacterial, antiviral, anti-mycotic or anti-parasitic activity and the like. The pharmaceutical agent or agents will become trapped in the composition upon its formation and be released from the composition immediately or over a period of time.

Since the typical offending pathogen in mastitis is bacterium, the sol-gel polymer composites may desirably contain the antibacterial agent. There are a variety of antibacterial agents available for use in animals. These antibacterial agents include, but are not limited to, the following: macrolides, for example, tulathromycin (Draxxin®), tildipirosin (Zuprevo®), tilmicosin (Micotil®), tylosin phosphate (Tylan®), and gamithromycin (Zactran®); cephalosporins, for example, ceftiofur sodium (e.g., Naxcel® and Excenel®), ceftiofur hydrochloride (e.g., Excenel RTU®, Excenel RTU EZ®, Spectramast®), ceftiofur crystalline free acid (Excede®), cefovecin sodium (Convenia®), and cefpodoxime proxetil (Simplicef®); lincosaminide antibiotics, for example, lincomycin (Lincomix®), pirlimycin hydrochloride (Pirsue®), and clindamycin hydrochloride (Antirobe®); fluoroquinolones, for example, danofloxacin (Advocin®), enrofloxacin (Baytril®), and marbofloxacin (Zeniquin®); and tetracyclines, for example, chlortetracycline, oxytetracycline, and doxycycline. Other antibacterial agents include, but are not limited to, a penicillin derivative such as amoxicillin trihydrate alone or with clavulonic acid (Clavamox®), spectinomycin (Adspec®), potentiated sulfonamides including trimethoprim/sulfadiazine (Tucoprim®) and sulfadimethoxine/ormetoprim (Primor®); chloramphenicol and its derivatives such as thiamphenicol and fluorinated synthetic analogs of thiamphenicol such as florfenicol (for example, Nuflor® and Nuflor® Gold). An antimicrobial agent may be administered simultaneously or sequentially with the compositions of the present disclosure.

According to some aspects, compositions in accordance with the present disclosure may include an immiscible mixture of a continuous aqueous sol-gel polymer phase and a discontinuous oil phase. As used herein, "continuous aqueous sol-gel polymer phase" refers to the portion of the emulsion in which the discontinuous oil phase is dispersed. Accordingly, a "discontinuous oil phase" refers to the multiplicity of discrete elements dispersed within, and immiscible with, the continuous aqueous liquid phase.

Stable oil-in-water emulsions in accordance with the present disclosure may include an oil, one or more emulsifiers and a sol-gel polymer composite, where the sol-gel composite is present from about 55% to about 90% by volume of the emulsion and where the oil is present in an amount from about 10% to about 45% by weight of the emulsion.

An "emulsifier" refers to a material that promotes the stability of an oil-in-water emulsion such that the discontinuous oil phase remains substantially dispersed within the continuous aqueous liquid phase. Generally, an emulsifier is at least partially soluble in at least the continuous aqueous liquid phase or the discontinuous oil phase. According to some embodiments, an emulsifier is partially soluble in both the continuous aqueous liquid phase and the discontinuous oil phase. The emulsifiers used in accordance with the present disclosure may include amphiphilic surfactants, or a combination or hydrophilic and hydrophobic surfactants. Emulsifiers of particular interest include, but are not limited to, gum acacia, modified gum acacia, a lecithin, agar, ghatti gum, modified ghatti gum, pectin, carrageenan, a xanthan gum, a modified starch, particularly a modified food starch (for example, a modified corn starch), a modified alginate (e.g., esters of alginic acid such as propylene glycol alginate), polyoxyethylene sorbitan, a polyoxyethylene sorbitan ester (e.g., Polysorbate 20, Polysorbate 80, and the like), a sugar ester (e.g., sucrose monostearate, and the like), and combinations thereof, a fatty alcohol (e.g., cetostearyl alcohol, cetearyl alcohol, cetylstearyl alcohol, and the like), mono- and/or di-glycerides, proteins and combinations thereof.

The sol-gel polymer composites of the disclosure can form durable seals or strong solids in response to one or more physiological stimulus, typically at a temperature of about 37° C. Ideally, a "strong" solid sol-gel polymer means that the elastic modulus G' (also referred to as the storage modulus (G')) is at least about 420 Pa or higher at physiological temperature. The "strong solid" is generally a gel or solid formed after the sol-gel phase transition for which G' at physiological conditions (e.g., 37° C., and/or near physiological pH) is generally above about 560 Pa, often about 600 Pa or higher, but also embracing from about 450 Pa to about 10,000 Pa and including, but not limited to, values of about 490 Pa, about 560 Pa, about 650 Pa, about 800 Pa, about 1700 Pa, about 1900 Pa, about 2500 Pa, about 5500 Pa about 6000 Pa, about 6500 Pa, about 7000 Pa, about 7500 Pa, about 8000 Pa, about 8500 Pa, about 9800, about 9000 Pa, about 9500 Pa, about 10,000 Pa or higher, and the like. In some embodiments, G' is from about 450 Pa to about 600 Pa, about 500 Pa to about 1000 Pa, about 1000 Pa to about 6000 Pa, about 5000 Pa to about 9800 Pa, about 7000 Pa to about 10,000 Pa, from about 8500 Pa to about 10,000 Pa, etc.

The "strong" solid sol-gel polymer composite of the disclosure is generally stronger than known chitosan hydrogels, which are known to be weak (in other words, a strong solid sol-gel polymer composite has stronger or higher mechanical properties than known chitosan hydrogels). In other embodiments, the G' of the sol-gel polymer composite useful as a teat sealant may be from about 420 Pa to 9,800 Pa or above, wherein the polymer composite has been unexpectedly found to be infusible without leakage and to form a durable seal in reaction to physiological stimuli similar to the stronger polymer composites described herein.

Advantageously, the sol-gel polymer composites possess thermal thickening properties making them capable of gelling or solidifying quickly in response to one or more physiological stimulus, such as physiological temperatures, to form a long-lasting seal or a strong solid without the addition of any other agents. Moreover, the sol-gel polymer composites gel or solidify very rapidly in response to one or more physiological stimulus and form the seal or solid mass having mechanical or viscoelastic properties as discussed herein, wherein the solid possesses sufficient strength to uniquely enable it to withstand mechanical or hydraulic pressures under physiological conditions in the animal. In some instances, the sol-gel polymer composites may gel or solidify in seconds, i.e., instantly or almost instantly, after exposure to the physiological stimulus, for example, after infusion into a dairy animal. The sol-gel polymeric composites provided herein undergo a liquid-solid phase transition so fast in response to physiological stimuli that a plug is rapidly formed at the site of injection. The sol-gel polymer composites show favorable shear-thinning properties, i.e., their viscosity will decrease upon increasing shear rate, which beneficially allow the sol-gel polymer composites to be capable of being easily infused or, before infusion, deformed in a syringe at room temperature, even if solidification has already occurred. Due to the beneficial shear-thinning properties, the sol-gel polymer composites can embrace solid structures having high porosity and/or elasticity for better manipulation of the material to seal the teat area yet to permit the release of pharmaceutical agents required for treatment of mastitis.

In contrast to the disadvantages of using weak gels known in the art that tend to spread and to leak in dynamic physiological environments, it is a further benefit of the present sol-gel polymer composite in its ability to solidify rapidly such that the composite can provide an instant-gelling, resilient seal or strong solid that permits easy infusion through a syringe without leaking or dripping and rapid formation of a no-leak, no-drip sol-gel plug after infusion into the teat canal or teat sinus of a dairy animal. In some instances, sol-gel polymer composites are capable of being administered with a single-barrel syringe.

Due to the properties of the sol-gel polymer formulations to respond to changes in temperature, pH and ionic strength, they can form long-lasting seals or strong gels/solids when no force is applied, but they can flow and are syringeable upon application of external force, e.g., in a syringe. The composites can also form a durable, elastic gel, foam or porous solid after infusion.

Other valuable technical effects that are seen in the specially designed sol-gel polymer composites are the ability to form hydrophobic substitution in the polymers to increase viscosity, microgel spheres capable of crosslinking in physiological fluids and microgel spheres capable of being used for drug release as well as to control the rate of degradation in an animal and to form a porous solid with a particular pore size in a subject and desirable viscoelastic properties at physiological temperature.

Beneficially, the water-based sol-gel polymer formulations are capable of being infused directly into the teat canal of the milk-producing animal and form a firm sealant during the dry period. The formulations can create this impermeable seal at 37° C. in the presence of milk and under high ionic content that is usually seen upon the drying off of the mammary gland.

Method for Making Sol-Gel Polymer Composites

Sol-gel processes are wet-chemical techniques widely used in the field of materials science and engineering. Such methods are used primarily for the fabrication of materials starting from a colloidal solution (sol) that acts as the precursor for an integrated network (or gel) of discrete particles or network polymers. In a sol-gel process, a fluid suspension of a colloidal solid (sol) gradually evolves towards the formation of a gel-like diphasic system containing both a liquid phase and a solid phase whose morphologies range from discrete particles to continuous polymer networks (for general information, see C. J. Brinker and G. W. Scherer, 1990, Sol-Gel Science: The Physics and Chemistry of Sol-Gel Processing, Academic Press, ISBN 0121349705; L. L. Hench and J. K. West, 1990, The Sol-Gel Process, Chemical Reviews 90:33).

In some instances, a reactivity and a functionality of a polymer can be altered by addition of a set of functional groups including, but not limited to, an acid anhydride, an amino or salt, an N-substituted amino, an amide, a carbonyl, a carboxy or salt, a cyclohexyl epoxy, an epoxy, glycidyl, hydroxy, an isocyanate, urea, an aldehyde, an ester, an ether, an alkyl, an alkenyl, an alkynyl, a thiol, a disulfide, a silyl or a silane, or groups selected from glyoxals, aziridines, active methylene compounds or other β-dicarbonyl compounds (e.g., 2,4-pentandione, malonic acid, acetylacetone, ethylacetone acetate, malonamide, acetoacetamide and its methyl analogues, ethyl acetoacetate, and isopropyl acetoacetate), a halo, a hydride, or other polar or H bonding groups and combinations thereof. Such functional groups can be added at various places along the polymer, such as randomly or regularly dispersed along the polymer, at the ends of the polymer, on the side, end or any position on the crystallizable side chains, attached as separate dangling side groups of the polymer, or attached directly to a backbone of the polymer. Also, a polymer can be capable of cross-linking, entanglement, or hydrogen bonding in order to increase its mechanical strength or its resistance to degradation under ambient or processing conditions.

As can be appreciated, a polymer can be provided in a variety of forms having different molecular weights, since a molecular weight (MW) of the polymer can be dependent upon processing conditions used for forming the polymer. Accordingly, a polymer can be referred to herein as having a specific molecular weight or a range of molecular weights.

The sol-gel polymer composites rely on fast, salt-induced and thermoreversible gelling systems based on chitosan that are formed by mixing chitosan with hydrophilic polymers (e.g., water-soluble polysaccharides) that create highly viscous thermosensitive gels. These water-swellable polymer composite formulations undergo a rapid gelation upon increasing temperature, pH and ionic strength. The composites typically contain two hydrophilic polymers and ionic gelators. The first polymer undergoes temperature-induced gelation and enables formation of an elastic gel in the teat canal at physiological temperatures, e.g., at about 37° C. The second polymer forms a gel upon contact with ionic gelators (gelation agents) introduced to the formulation. With the addition of the gelation agent (i.e., a thermogelling element), the system creates physical crosslinking. The gelation is basically due to physical conformational changes in the polymers that are the major ingredients in the product, with no covalent crosslinking bonds between polymers being formed. The strength of the gel of the second polymer depends on the amount of gelator added, as well as pH and ionic strength of the formulation, which typically has a pH of about 5.1 to 6.8 and an ionic strength of about 5 g/L. The two hydrophilic polymers have a profound effect on the gelation of chitosan, leading to a fast response to stimuli such as salt addition and body temperature. As a result, the gels are reinforced upon changes of pH and ionic content in the drying teat canal.

By carefully adjusting polymer, salt, and gelation agent concentrations in the system, it is possible to fine-tune the gelation temperature and the mechanical properties or integrity of the system, both below and above the gelation threshold, including the speed and reversibility of gel formation under physiological conditions (e.g., temperature), as well as the biocompatibility, the viscoelastic properties (e.g., G'), the permeability/porosity of the system and the durability of the seal or strong solid that is formed after gelation. For example, the polymer, salt addition and the gelation agent can be manipulated to make the sol-gel polymeric composites suitable for specially designed human or veterinary uses which require a macroporous solid with a specific pore size and having durable, elastic properties, or in applications that require structures that are solid with a high porosity or with a particular pore size to allow free passage of biomolecules such as antibiotics.

Moreover, the sol-gel polymer formulations can be preferentially designed for compatibility and use with cheese starter cultures, for example, *Lactococcus lactis, L. lactis* subsp. *cremoris, Streptococcus thermophilus*, and the like. Since the live starter culture needs to achieve proper acidification for the process of making cheese to work, the polymer formulations' acidity can be suitably adjusted by altering the salt component to avoid interfering with culture activity and growth. Thus, to make the sol-gel polymer formulations beneficially compatible with cheese starter cultures, the salt component is easily varied to neutralize the acidity of the final product. Typically, for instance, the formulation at a pH of approximately 6.8 (relatively neutral), does not inhibit standard bacterial cultures and would find use with cheese starter cultures.

To illustrate certain formulations of this disclosure, the sol-gel polymer composite comprises about 7.3% w/w methyl cellulose, about 1.8% w/w chitosan, about 9.4% w/w sodium pyrophosphate tetrabasic (as solution salt), about 0.05% w/w sodium pyrophosphate tetrabasic (as solid salt), and about 82% w/w 0.1 M aqueous acetic acid. This composite is referred to herein as the "F1" or "F1-20141210" formulation. In a second embodiment, the sol-gel polymer composite comprises about 7.3% w/w methyl cellulose, about 1.8% w/w chitosan, about 9.1% w/w β-Glycerophosphate disodium (as solution salt), about 3.0% w/w β-Glycerophosphate disodium (as solid salt), and about 82% w/w 0.1 M aqueous acetic acid. This composite is referred to herein as the "F4" or "F4-20141210" formulation. For comparison, other sol-gel polymer composites were prepared, such as the F2 or the F3 formulations shown in the below Tables B and C. In further instances, the sol-gel polymer composite comprises about 16% w/w, 17% w/w or 18% w/w Pluronic® F127 in a 0.5% w/w, 1% w/w, or 2% w/w chitosan solution in acetic acid. In another embodiment, the sol-gel polymer composite comprises one of the chitosan-Pluronic® F127 solutions set forth in the below Table 4.

As a general rule, the amounts of the ingredients in the sol-gel polymer composite formulations of the present disclosure may vary somewhat. In the above illustration of the F1 to F4 formulations, for example, the amount of the methyl cellulose may range between about 4% w/w to about 12% w/w, the chitosan may range between about 0.5% w/w to about 4% w/w, the solution salt or gelling agent may range between about 6% w/w to about 12% w/w, the solid salt may range between about 0.01% w/w to about 4% w/w, and higher concentrations than 0.1M of the aqueous acetic acid may be used. It should nevertheless be appreciated that the ranges of certain combinations may be readily adjusted, including higher or lower amounts than the stated ranges, in order to form a gel or a hydrogel having the desired properties described herein.

Uses of Sol-Gel Polymer Composites

The sol-gel polymeric composites provided herein undergo a liquid-solid phase transition in response to one or more physiological stimulus. They may have use therefore in a wide range of animal and human health applications where it is desirable to inject a liquid that solidifies rapidly after injection in a subject. In particular, sol-gel polymer composites may have use in applications where it is desirable to be provided with solid structures that have high porosity, elasticity or sufficient strength to withstand mechanical or hydraulic pressures under physiological conditions in a subject.

It should be understood that suitability of sol-gel polymer composites for a particular application will be dictated by numerous factors, such as their biocompatibility, mechanical integrity, speed and reversibility of gel formation under physiological conditions (e.g., temperature), mechanical or viscoelastic properties (e.g., G'), porosity/permeability, and durability. In accordance with the present technology, such properties can be determined by adjusting polymer and gelation agent concentrations in the system, as described herein. For example, in some embodiments sol-gel polymer composites are suitable for use in applications that require a macroporous solid with a specific pore size and having durable, elastic properties, or in applications that require structures that are solid with a high porosity or particular pore size to allow free passage of biomolecules such as glucose, oxygen, or insulin.

In some embodiments, sol-gel polymeric composites are suitable for use in applications that require formation of no-leak, no-drip plugs inside orifices in a subject. For example, they would find use as mucoadhesive implants, ocular drops, transdermal patches, dental implants, vaginal suppositories, etc., which need no-leak, no-drip plugs, as do artificial spinal disks and cartilage.

For other embodiments, the sol-gel polymeric composites are suitable for use in tissue engineering where the implant can replace deteriorated or otherwise damaged cartilage within a joint. In this regard, the composites are suitable for use as artificial cartilage. Since cartilage tissue is important for normal joint function, there is a need for artificial cartilage for therapeutic uses to replace tissue damaged from injury or aging. Potential materials for use in artificial cartilage need to be viscoelastic, strong, and durable, like the sol-gel polymeric composites provided herein. Sol-gel polymeric composites may, therefore, be used for joint surgery, implanted in a knee joint, used as cornea repair material, or used for repairing, replacing, or therapeutically treating tissues and body parts. Sol-gel polymeric composites may form a durable, elastic gel after injection and in the presence of ions in the synovial fluid and bone, forming an artificial cartilage, meniscus or nucleus pulposus.

The composites are also beneficially useful as injectable implants to treat osteoarthritis, rheumatoid arthritis, other inflammatory diseases, generalized joint pain or other joint diseases, for wound healing, or as suppositories. In some embodiments, sol-gel polymeric composites may be injected to rapidly form a plug in a subject, particularly where the liquid-solid transition occurs so quickly in response to physiological stimuli that a plug is instantly formed at the site of injection. Sol-gel polymeric composites may, for example, be injected into Islets of Langerhans in the pancreas in order to immune-isolate the islet cells and allow free passage of glucose and oxygen.

In certain embodiments, sol-gel polymeric composites are useful as embolic or occlusion agents, e.g., to block arteries or to starve cancer cells. In other embodiments, sol-gel polymeric composites are useful as ultrasound contrast agents. In yet other embodiments, sol-gel polymeric composites are suitable for injection along with cells that can form a macroporous or microporous substrate, for tissue engineering.

Alternative embodiments find that the sol-gel polymeric composites are suitable for use as a bulking agent for reconstructive or cosmetic surgery, for drug delivery systems, e.g., as a platform for slow-release delivery of therapeutic agents, or for treatment of varicose veins, e.g., forming an injectable foam. In some embodiments, sol-gel polymeric composites are suitable for use as bulking agents to treat uterine fibroids or as dental implants. The composites are further suitable for use in staunching wounds, e.g., forming a porous solid after injection that serves to block blood flow e.g. to block dental tubules, and as brain implants, and as film-forming polymers on teeth.

Sol-Gel Polymer Composites as Teat Sealants for Animals

It should be understood that desired characteristics of the teat sealant encompassing the sol-gel polymer composites of the present disclosure will vary depending upon the intended usage of the sealant, such as where it will be applied (e.g., exterior mammary tissue or within the teat cavity), the formulation of the sealant and other factors. However, some general characteristics of the teat sealant can be stated. Where the sealant is placed intramammary in the teat canal, for instance, the tailorable shear thinning characteristic allows for ease of infusion as well as removal by manual stripping from the teat canal. It is advantageous that the adhered teat sealant is easily removable from the teat. By adjusting the formulation of the teat sealant, the sol-gel polymer composites can be made strong enough such that the sealant can be readily peeled off the teat and removed in one cohesive unit in the first strip leaving little to no material behind. When the sol-gel polymer composites are used as plugs at the macro or micro level, they can be formulated to embrace an appropriate range of adhesion which allows the in situ formed compositions to adhere to tissue and to stay in place as long as necessary while still being easily removed manually from the site. In addition, if these compositions are plugged in a location where a barrier to retain or absorb fluid is necessary, the composition can be formulated to absorb the fluid naturally while remaining in their desired location.

It is further advantageous that the in situ formed teat sealant of the present disclosure is conformable to the shape of the teat or teat canal. The pliability property of the sol-gel polymer composite allows the sealant to conform to the topography of the teat surface or canal as well as the tissue surface around the teat for a good fit. Such conformability also extends the longevity, comfort and efficacy of the teat sealant.

The sol-gel polymeric composite useful as a teat sealant in the disclosure is also safe and stable. The nontoxic property of the sealant provides safety to the target animal as well as the human handler of the animal and applier of the sealant on the animal. Because the teat sealant causes no residual accumulation of sealant in milk lines or related parlor equipment, the nontoxicity of the sealant also ensures that human food products, such as the milk and milk products made from the milk obtained from the treated animals, are safe to consume. In some instances, all of the composition ingredients are non-heavy metal in nature, biocompatible, biodegradable tissue-adherent and nonirritating to the animal in the amounts present in the final teat sealant formulations. While in other instances, the composition ingredients may include non-biodegradable synthetic materials. Since the sol-gel polymer composites are suitable for infusion into the mammary gland of the animal, they may be made free of toxic materials, irritants, etc., and suitable for use under physiological conditions of temperature, pH, ionic strength, etc. Moreover, the sol-gel polymer composites can be readily sterilized by standard steam, dry sterilizers (autoclaves), gamma irradiation, electron beam methods (e-beam sterilization) and the like. Preservatives can also be included in the composition without altering the beneficial properties of the teat sealant.

Depending on the delivery method, the viscosity is specially designed in the formulation of the teat sealant to be made suitable for topical application, infusion and the like. Thus, the viscosity of the sol-gel polymer composites is controlled so that the composition can be sprayed or streamed onto or into the teat in such a way that an excellent barrier is created. The sol-gel polymer composites are also readily passed through a syringe and have excellent shear-thinning properties which are necessary for molding the composite in a syringe at room temperature for quick and easy product use by the animal handler. In particular, the sol-gel polymer composite is beneficially capable of being infused using a single-barrel syringe. When infused directly into the teat, the formulations have the ability to fill the teat canal and rapidly transition to a gel at body temperature. The shear thinning property of the formulations allows both ease of infusion and removability.

Gelation of the composition on the teat is preferably rapid, to avoid run off or loss of the composition from the place of application. The gelling time can be about 5 minutes or less, preferably less than about three minutes, more preferably less than about 30 seconds, and, in some situations, as low as about 10 seconds or less, especially with external application of the sol-gel polymer composites.

Several of the desired, aforementioned characteristics of the teat sealant useful in the present disclosure are obtained by adjusting polymer and gelation agent concentrations in the sol-gel polymer composite to modify the mechanical properties and permeability/porosity of the durable seal or strong solid. Basically, the adhesion and the swelling properties of the teat sealant are controlled by specially designing the formulation. The sol-gel polymer composites, which possess a specific combination of adhesion and swelling properties, exhibit incomparable and new properties such as adhering to the animal's tissue for an extended time period yet being easily removed as a teat barrier when the prophylactic treatment is finished, or being strong enough to be peeled off the animal's teat in one piece or easily removed as a semi-solid or liquid yet being flexible enough to conform to the animal's body for comfort and remain in place as an effective barrier to prevent or to reduce the incidence of mammary disorders.

Delivery of the Teat Sealant Compositions

Appropriate viscosity depends upon the delivery means to be employed. Generally, the composition should have a viscosity lower than about 800 cps at room temperature or during conditions of use (that is, not in the animal), preferably lower than 300 cps, more preferably lower than 200 cps to be delivered via aerosol. Delivery through a pump spray normally requires a lower viscosity, such as less than about 150 cps. Spray without aerosol calls for a viscosity less than about 50 cps.

The teat sealant formulation is applied to the teat by conventional means such as, for example, a spray or stream from a syringe, pump, spray nozzle, aerosol, dip, or other type of device. A combination of the spray and stream may be applied in a method similar to a shower head, whereby multiple streams provide the simulated broad coverage of a spray application. The sol-gel polymer composites are sprayed or streamed externally onto the teat tissue whereupon they form a barrier seal.

For application by infusion inside the teat, as in the teat sinus or cistern, any veterinary syringe having a tapered syringe end, a teat needle or intramammary tip made especially for insertion of solutions in to the teat canal may be used. For an example, the gels can be inserted through a conventional infusion cannula or infusion nozzle using a standard 5 or 6 mL syringe. An effective amount of the teat sealant that will form the desired physical barrier in a teat canal in order to prevent or treat a mammary disorder depends upon the dairy animal species and size of its teats. Typically, a volume of between 2 and 3 mL is satisfactory to adequately fill the teat canal but the amount may vary and can be easily titrated by the handler infusing the sealant into the teat.

Generally, about 0.5 to 5.0 mL of the composition will be administered to an animal teat, preferably about 1.0 to 4.0 mL, more preferably about 2.0 mL or higher, and even more preferably about 3.0 mL. Formulations may be pre-loaded into syringes for easy unit dose administration. Desirably, the composition is administered when the dairy animal enters into the dry period at the end of the lactation cycle or during the dry period of the animal, especially when it is a heifer or cow.

The composition may also be delivered externally or topically to the teat from a spray device or a stream device. The spray device may include a container having a dispenser for spray delivery of the liquid composition. The type of container used is variable, depending upon compatibility with the composition and the spray dispenser and can be glass, plastic, or metal. If the solutions are of a low enough viscosity, a spray delivery may be achieved with simple mechanical forces such as those achieved when depressing the plunger of a syringe by hand through an appropriately designed nozzle. It may be desirable to apply several layers of the composition to the teat to ensure adequate coverage of the teat. In any case, an effective amount for forming the physical barrier can be readily determined by visual appearance of the sealant on the teat.

The composition can also be delivered using a syringe outfitted with a spray head. Generally, any chemical, mechanical or electronic method for propelling the liquid composition as a spray from the container is appropriate. In one aspect, a compatible liquid or gaseous aerosol propellant is placed in an appropriate container along with the composition and the dispenser includes a valve mechanism that enables atomized spray delivery of the liquid composition. Desirably, an intramammary infusion device may be used to deliver the teat sealant composition directly to the teat. The device can have a single dispenser, such as a spray tip from Nordson Corporation (Westlake, Ohio, U.S.A.). The device may include a meter so that the quantity of composition can be controlled.

Examples of devices that could be used, or modified for use, to deliver the compositions as teat sealants include those described in WO 2015/038281 (Zoetis), U.S. Patent Application No. 2015/0080841 (C. M. Bradley et al.), U.S. Pat. No. 5,989,215 (Y. Delmotte et al.), U.S. Pat. No. 8,353,877 (S. Hallahan et al.), WO 2003/022245 (Bimeda Research & Development Limited), and WO 2013/021186 (Norbrook Laboratories Limited).

The foregoing description shows how to make the new sol-gel polymer composite formulations as well as their unique properties for use in the present disclosure. The following examples demonstrate other aspects of the disclosure. However, it is to be understood that these examples are for illustration only and do not purport to be wholly definitive as to conditions and scope of this disclosure. Chemicals were purchased from Sigma-Aldrich in St. Louis, Mo. unless indicated otherwise. It should be appreciated that the sequence of steps in the preparation of the sol-gel polymer composites is not critical and may be varied from the examples. For instance, the order in which the ingredients are introduced into a tank can be altered (such as adding the methyl cellulose first instead of adding chitosan first and the like) without detriment to the final product. It should be further appreciated that when typical reaction conditions (e.g., temperature, reaction times, etc.) have been given, the conditions both above and below the specified ranges can also be used, though generally less conveniently. Except as otherwise indicated, the examples are conducted at room temperature (about 23° C. to about 28° C.) and at atmospheric pressure. All parts and percentages referred to herein are on a weight basis and all temperatures are expressed in degrees centigrade unless otherwise specified.

A further understanding of the disclosure may be obtained from the non-limiting examples that follow below.

Example 1

Preparation and Properties of Sol-Gel Polymer Composites

Four polymer composite formulations (F1, F2, F3, and F4) were prepared as follows below. Tables A, B, C, and D show the F1, F2, F3, and F4 formulations respectively. Formulations were prepared in batches of about 30 g, 110 g, or 165 g, as indicated in the tables.

TABLE A

F1 Formulation

| Substance | Weight (g) | Solid (g) | % Solid | chitosan/gelator (w/w) | Comments |
|---|---|---|---|---|---|
| methyl cellulose | 12 | 12.000 | 7.251% | 38.70967742 | viscous clear liquid, pH 6, viscosity decreased upon autoclaving |
| chitosan | 3.0 | 3.000 | 1.813% | | |
| sodium pyrophosphate tetrabasic (as 5 g/L solution) | 15.5 | 0.078 | 0.047% | | |
| 0.1M aq. acetic acid | 135.0 | | | | |
| Total | 165.5 | 15.1 | 9.110% | | |
| methyl cellulose | 8 | 8.000 | 7.271% | 40 | viscous clear gel, pH 6 |
| chitosan | 2.0 | 2.000 | 1.818% | | |
| sodium pyrophosphate tetrabasic (as 5 g/L solution) | 10.0 | 0.050 | 0.045% | | |
| 0.1M aq. acetic acid | 90.0 | | | | |
| Total | 110.0 | 10.1 | 9.157% | | |
| methyl cellulose | 2.4 | 2.400 | 8.000% | 40 | viscous clear liquid, pH 6, viscosity decreased upon autoclaving |
| chitosan | 0.6 | 0.600 | 2.000% | | |
| sodium pyrophosphate tetrabasic (as 5 g/L solution) | 3.0 | 0.015 | 0.050% | | |
| 0.1M aq. acetic acid | 24.0 | | | | |
| Total | 30.0 | 3.0 | 10.050% | | |

TABLE B

F2 Formulation

| Substance | Weight (g) | Solid (g) | % Solid | chitosan/gelator (w/w) | Comments |
|---|---|---|---|---|---|
| methyl cellulose | 2.4 | 2.400 | 8.000% | 2 | white elastic paste, pH 7, viscosity decreased upon autoclaving |
| chitosan | 0.6 | 0.600 | 2.000% | | |
| potassium phosphate dibasic trihydrate (as 100 g/L solution) | 3.0 | 0.300 | 1.000% | | |
| 0.1M aq. acetic acid | 24.0 | | | | |
| Total | 30.0 | 3.3 | 11.000% | | |
| methyl cellulose | 8 | 8.000 | 7.271% | 2 | white elastic paste, pH 7, viscosity decreased upon autoclaving |
| chitosan | 2.0 | 2.000 | 1.818% | | |
| potassium phosphate dibasic trihydrate (as 100 g/L solution) | 10.0 | 1.000 | 0.909% | | |
| 0.1M aq. acetic acid | 90.0 | | | | |
| Total | 110.0 | 11.0 | 10.020% | | |

TABLE C

F3 Formulation

| Substance | Weight (g) | Solid (g) | % Solid | chitosan/gelator (w/w) | Comments |
|---|---|---|---|---|---|
| methyl cellulose | 2.4 | 2.400 | 8.000% | 3.8 | Opaque gel, pH 7, viscosity decreased upon autoclaving |
| chitosan | 0.6 | 0.600 | 2.000% | | |
| sodium pyrophosphate tetrabasic/potassium phosphate dibasic trihydrate (as 2.5 g/L and 50 g/L solution) | 3.0 | 0.158 | 0.525% | | |
| 0.1M aq. acetic acid | 24.0 | | | | |
| Total | 30.0 | 3.2 | 10.525% | | |
| methyl cellulose | 8 | 8.000 | 7.271% | 2 | white elastic paste, pH 7, viscosity decreased upon autoclaving |
| chitosan | 2.0 | 2.000 | 1.818% | | |
| sodium pyrophosphate tetrabasic/potassium phosphate dibasic trihydrate (as 2.5 g/L and 50 g/L solution) | 10.0 | 0.525 | 0.477% | | |
| 0.1M aq. acetic acid | 90.0 | | | | |
| Total | 110.0 | 10.6 | 9.589% | | |

TABLE D

F4 Formulation

| Substance | Weight (g) | Solid (g) | % Solid | chitosan/gelator (w/w) | Comments |
|---|---|---|---|---|---|
| methyl cellulose | 12 | 12.000 | 7.273% | 0.6 | Opaque gel, pH 7, phase separation may occur during sterilization |
| Chitosan | 3.0 | 3.000 | 1.818% | | |
| β-Glycerophosphate disodium (as 44% aqueous solution) | 15.0 | 4.884 | 2.960% | | |
| 0.1M aq. acetic acid | 135.0 | | | | |
| Total | 165.0 | 19.9 | 12.051% | | |
| methyl cellulose | 2.4 | 2.400 | 8.000% | 0.6 | Opaque gel, pH 7, phase separation may occur during sterilization |
| chitosan | 0.6 | 0.600 | 2.000% | | |
| β-Glycerophosphate disodium (as 44% aqueous solution) | 3.0 | 0.977 | 3.256% | | |
| 0.1M aq. acetic acid | 24.0 | | | | |
| Total | 30.0 | 4.0 | 13.256% | | |
| methyl cellulose | 8 | 8.000 | 7.271% | 0.6 | Opaque gel, pH 7 |
| chitosan | 2.0 | 2.000 | 1.818% | | |
| β-Glycerophosphate disodium (as 44% aqueous solution) | 10.0 | 3.256 | 2.959% | | |
| 0.1M aq. acetic acid | 90.0 | | | | |
| Total | 110.0 | 13.3 | 12.071% | | |

The F1 and F4 formulations were prepared as follows: First, 0.1 M AcOH was prepared by adding 0.813 g (0.772 mL) of AcOH to 135.5 mL of water for F1. For F4, 0.81 g (0.77 mL) of AcOH was added to 135.0 mL of water. Next, a solution of methyl cellulose (12 g), chitosan (3 g) in 0.1 N (0.1 M) AcOH (135.5 mL for F1 and 135.0 mL for F4) was prepared. The solution was prepared by addition of polymer powders to 0.1 N (0.1 M) AcOH heated to 85-90° C. with vigorous stirring. Heating was continued until a homogeneous dispersion was obtained (about 5 min.). The solution was then cooled to room temperature with stirring (300 rpm). Upon cooling, the solution clarified and became very viscous, necessitating reduction of stirring speed to 60-100 rpm. Cooling and clarification took about 1 hour. The solution was then stored at 4° C. until future use.

Solution of gelling agent (salt works in formulation as gelation agent, also referred to herein as "gelator" agent) in water was then prepared by mixing salt in powdered form with water. The concentrations for salt solutions were as follows: For F1, sodium pyrophosphate tetrabasic (5 g/L) was prepared by adding 100 mg of sodium pyrophosphate tetrabasic into 20 mL of water and stirring it until completely dissolved. For F4, β-glycerophosphate disodium hydrate (as 44% w/w aqueous solution) (44 g per 66 g of water) was prepared by adding 22 g of β-glycerophosphate disodium hydrate (as 44% w/w aqueous solution) into 33 mL of water and heated at 45° C. with stirring until completely dissolved.

Gelator solution thus prepared was added to cold polymer solution with slow mechanic stirring (with a mixer at 100 rpm) until homogeneous. Significant viscosity enhancement and bubble formation was observed. The solution was then left to rest overnight at 4° C. Formulations were sterilized by autoclaving on the liquid cycle.

The F2 and F3 formulations were prepared as follows: 0.1 M AcOH was prepared by adding 0.6 g (0.57 mL) of AcOH to 100 mL of water. A solution of methyl cellulose (8 g), chitosan (2 g), and sodium azide (0.025 g) was prepared in 0.1 N AcOH (90 mL). The beaker with the stirrer bar was weighed. Solution was prepared by addition of powders (one shot) to 0.1 N AcOH heated to boiling (85-90° C.) under stirring. Heating was stopped and a homogeneous dispersion was obtained by stirring with a spatula for about 3 min. This was completed with addition of AcOH until final weight (without salt) was achieved. The solution was then cooled to room temperature. Upon cooling, the solution clarified and became very viscous. Cooling and clarification took about 1 hour. The beaker was covered with parafilm and stored at 4° C. for 24 hours (or until further use).

A solution of gelling agent (salt as gelation agent or gelator) was then prepared in water by mixing salt in powdered form with water to the desired concentration. Gelation solution was added to the cold polymer solution under slow mechanical stirring (with a spatula or a mixer at 100 rpm). A significant viscosity enhancement and bubble formation was observed. The solution was left to rest overnight at 4° C. The solution was centrifuged at 4000 rpm for 10 min. in order to eliminate air bubbles.

Several polymers were tested at various concentrations in the formulations to select most favorable polymers and concentrations thereof for formulation performance. Various gelation agents were also tested to tune the temperature responsiveness of the formulation, its syringeability, and its flow properties. Four sol-gel polymer composite formulations (F1-F4) having a broad range of flow properties were then selected for further testing.

Preliminary characterization of the F1-F4 samples is shown in Table E. Note the pH of the gels was between about 6 and 7. In this experiment, it was shown that the gels could be injected through a standard 16-gauge needle using a 6 mL syringe, which demonstrates their unique ability to be infused through a teat needle or nozzle for use as teat sealants. For the data in Table E, the formulations tested were those prepared using the ingredients and the amounts in Tables A-D for 110 g total.

TABLE E

Properties of the Polymer Composite Formulations F1-F4

| Formulation | Solid content (%) | pH | Appearance (25° C.) | Syringeability (25° C.) | Plug formation in the presence of milk (37° C.) |
|---|---|---|---|---|---|
| F1 | 9% | 6 | Transparent gel | + | + |
| F2 | 10% | 7 | Off-white gel | + | + |
| F3 | 10% | 7 | Opaque gel | + | + |
| F4 | 13% | 7 | Opaque gel | + | + |

Plug formation in the presence of milk was tested by adding the formulations (1.5-2 mL) into test tubes containing 0.5 mL of milk (3.5% fat) at 37° C. All the formulations formed a gel plug on the surface of milk. The inspection of the interface between milk and gels showed that while some degree of mixing between formulations and milk was expected upon addition of the gel to the milk, the samples unexpectedly showed very limited miscibility with milk upon formation of the plug. The results indicated that the formulations were able to form a gel in the presence of milk and prevent leakage from the test tubes.

Figure 6:
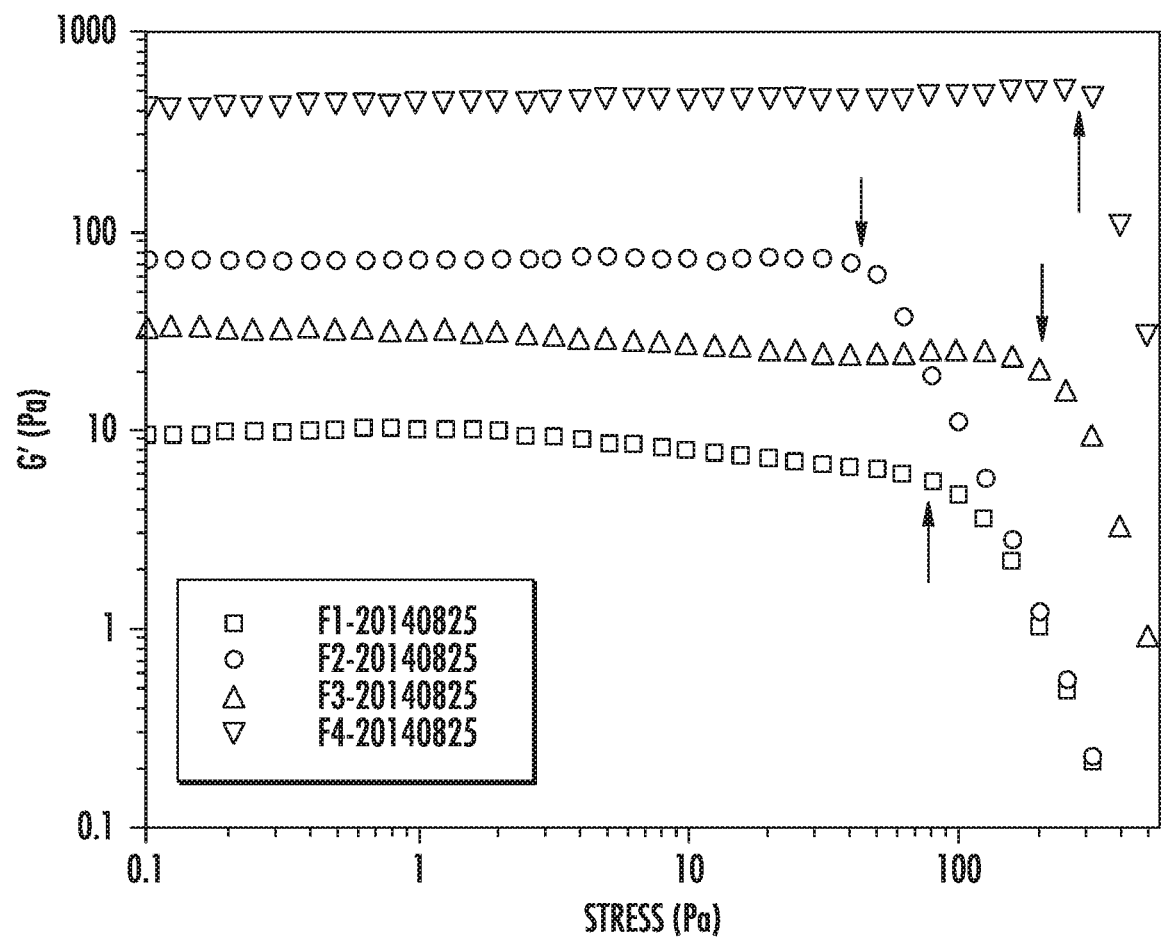
FIG. 6 shows stress sweep results for sol-gel polymer composite formulations F1-F4, as indicated, at oscillation frequency f=0.1 Hz and temperature T=25° C. The arrows indicate the beginning of the shear-thinning region.

A stress sweep test (i.e., measurements of elastic and loss moduli as a function of stress at fixed frequency) was performed to confirm shear-thinning character of the samples. The results are shown in FIG. 6. For the data in FIG. 6, the formulations tested were those prepared using the ingredients and the amounts in Tables A-D for 110 g total.

At low applied stresses, the values of elastic modulus G' were constant. The elasticity of samples covered a broad spectrum, ranging from about 10 Pa for F1 to about 440 Pa for F4. Shear-thinning behavior (i.e., a decrease of elastic modulus G' as a function of the applied stress) was observed at higher stress values. The shear-thinning region started at lowest stress for the F2 formulation, followed by F1, F3, and F4. These results confirm that the samples are syringeable and their infusion is possible. Since the force applied during formulation infusion and post-treatment teat stripping is well above 300 Pa, all formulations would not undergo any delivery or recovery issues.

Figure 7:
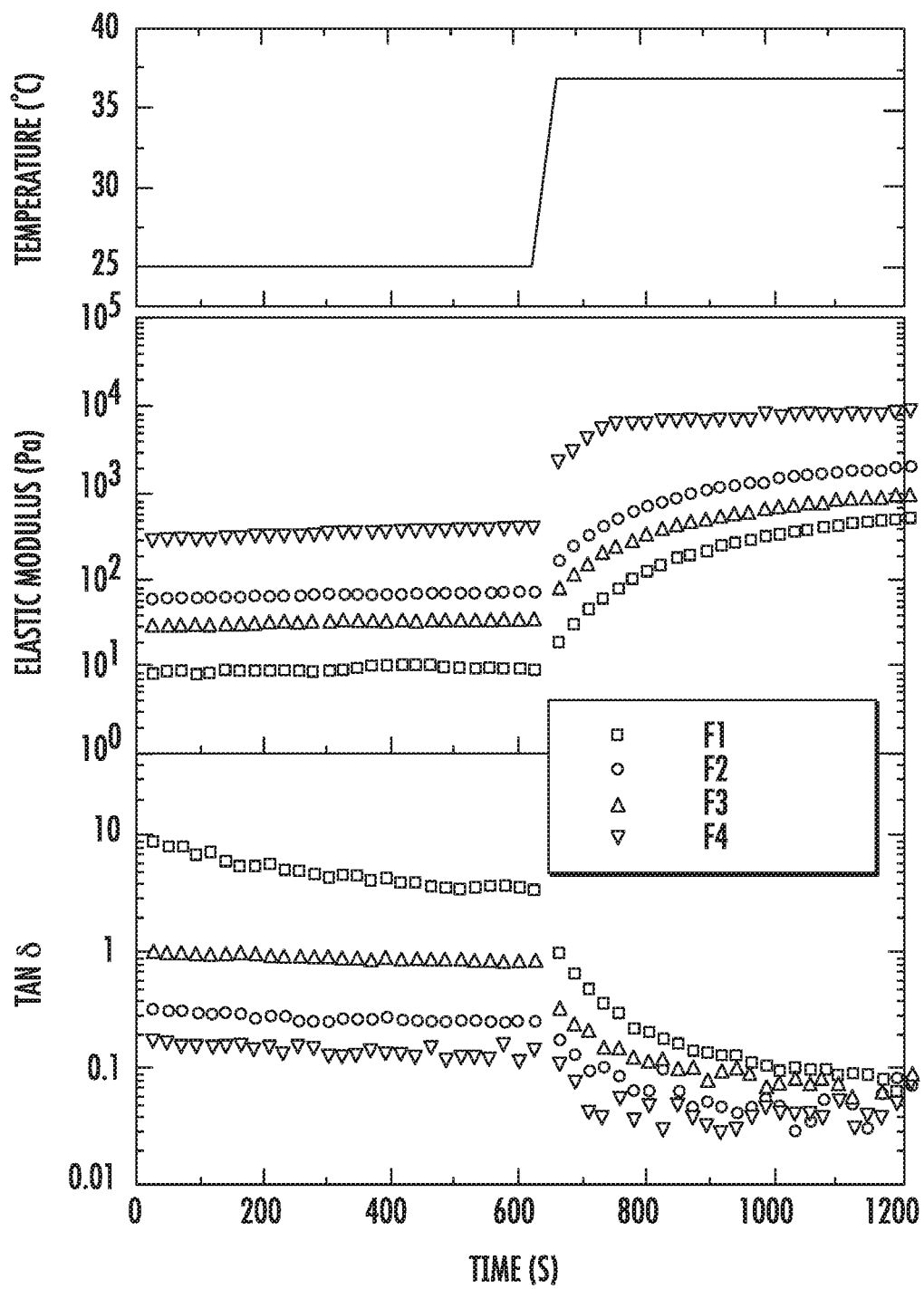
FIG. 7 shows time dependence of elastic modulus G' and loss tangent, tan $\delta$=G"/G', upon a temperature jump from 25 to 37° C. recorded at f=1 Hz and oscillatory stress of $\tau$=1 Pa.

Next, the rheology of the formulations was monitored upon a sudden jump in temperature from room to body temperature. The values of elastic and storage moduli as a function of time at a constant stress of 1 Pa (i.e., in the plateau region) and frequency (f=0.1 Hz) were followed. In the first step of the experiment (10 min.), the temperature was kept at 25° C. In the second step (10 min.), the temperature was fixed at 37° C. The heating process between both steps took around 20 seconds. The results are shown in Table F and FIG. 7; they are expressed as elastic modulus G' and loss tangent tan δ=G"/G', the ratio of elastic and viscous properties showing which one is dominant. With a tan δ value of 1, the elastic and viscous properties of the material are equal. The smaller the loss tangent, the more elastic is the material. For physical gels, G'>G" and tan δ<1. For viscous liquids, G">G' and tan δ>1. For the data in Table F and FIG. 7, the formulations tested were those prepared using the ingredients and the amounts in Tables A-D for 110 g total. It will be understood that values can vary based on equipment and the rheology methods employed; and, further, these values are relative from each other depending on the particular testing protocols.

TABLE F

Results of Rheological Tests for Sol-Gel Polymer Composite
Formulations F1-F4 (Values for G' and tan δ were
recorded 10 min. after the application of the stress. Angular
frequency f = 0.1 Hz, oscillatory stress τ = 1 Pa)

| Formulation | T = 25° C. | | T = 37° C. | | |
|---|---|---|---|---|---|
| | G' (Pa) | tan δ | G' (Pa) | tan δ | G'(37° C.)/G'(25° C.) |
| F1 | 9.3 | 3.4 | 490 | 0.08 | 53 |
| F2 | 71 | 0.26 | 1900 | 0.06 | 27 |
| F3 | 32 | 0.84 | 870 | 0.05 | 27 |
| F4 | 420 | 0.13 | 8600 | 0.04 | 20 |

Elasticity of F1-F4 increased significantly with temperature, as evidenced by the values of the ratio of G'(37° C.)/G'(25° C.) (Table E) that changed from 53 (F1) to 20 (F4). At room temperature, F1 behaved like viscous liquid (tan δ>1). Three other formulations showed solid-like behavior that became more pronounced in the order F3<F2<F4.

At 37° C., elastic modulus increased significantly. This was accompanied by a fast decrease of loss tangent, indicating the reinforcement of the gel structure. This process took about 1-2 min. for F2, F3 and F4. It was slightly longer (about 5 min.) for the F1 formulation.

In conclusion, four sol-gel polymer composite formulations covering a broad range of flow properties were prepared and characterized. The polymer composite formulations undergo a rapid gelation upon increasing temperature, pH and/or ionic strength. The composites contain two hydrophilic polymers and ionic gelators. As described, the first polymer undergoes temperature-induced gelation and enables formation of an elastic gel at about 37° C. The second polymer forms a gel upon contact with ionic gelators introduced to the formulation. The strength of the gel of the second polymer depended upon the amount of gelator added, as well as pH and ionic strength of the formulation.

The samples were infusible due to their shear-thinning properties. They showed temperature-induced thickening, i.e., their gel structure became stronger upon an increase of temperature. Results indicated that elasticity of the formulations, the onset of shear-thinning, the extent of temperature-induced thickening, as well as the time-scale of these processes depend on the gelation agent used in the formulation, potentially allowing for precise tuning of flow properties.

TABLE G

Combinations of Composite Formulations F1, F2 and F4

| | F1 | F2 | F4 |
|---|---|---|---|
| F3 | 50% | 50% | |
| F11 | 100% | 100% | |
| F12 | 50% | | 100% |
| F13 | 50% | | 50% |
| F14 | 100% | | 100% |
| F16 | 100% | 100% | 100% |

Additional formulations were prepared using combinations of the formulations F1, F2 and F4, as shown in Table G. These formulations vary by the amount and type of salt used as a cross-linker. The amounts were varied as a percent of the concentration used in the formulations as disclosed herein (i.e., 100% being the concentration disclosed, 50% being half the concentration) on the basis that F3 is a combination of 50% F1 salt and 50% F2 salt.

Example 2

Effect of Sterilization on Sol-Gel Polymer Composite Formulations

Autoclaving was tested as a method of sterilization. It is known that polymers similar to those used in the above formulations may undergo significant degradation upon sterilization with ionizing radiation or ethylene oxide. This degradation may be lessened by using high temperature to sterilize the samples.

Sterilization was performed at 121° C. during 10 min. The total length of the cycle, including heating and cooling parts was about 45 min. Table 1 shows a comparison of the properties of the formulations prepared with two different gelators (F1 and F4) before and after sterilization. For the data in Table 1, the formulations tested were prepared using the recipes in Tables A and D for 165.5 and 165 g total, respectively.

TABLE 1

Properties of Polymer Composite Formulations
Before and After Sterilization.

| Formulation | Conditions | pH | Appearance (25° C.) | Syringeability (25° C.) |
|---|---|---|---|---|
| F1-20141210 | Before sterilization | 6 | Transparent slightly yellowish gel | + |
| | After sterilization | 6 | Transparent yellowish viscous solution | + |
| F4-20141210 | Before sterilization | 7 | Opaque slightly yellowish gel | + |
| | After sterilization | 7 | Opaque yellowish gel | + |

After sterilization, all the formulations could be injected through a standard 16-gauge needle using a 6 mL syringe, which shows the formulations can be injected as teat sealants through a teat needle or nozzle. The pH of the formulations did not change significantly upon sterilization. However, visual observation indicated that both formulations showed a more pronounced yellow/brown color after autoclaving and that their flow properties changed. In the case of F1-20141210, there was a change from "gel" to "liquid" at 25° C.

Next, the changes in flow properties of the sterile and non-sterile formulations were monitored more closely upon a jump in temperature from 25° C. to 37° C. The values of elastic and storage moduli as a function of time were followed at a constant stress (1 Pa) and frequency (f=0.1 Hz). In the first step of the experiment (10 min.), the temperature was kept at 25° C. In the second step (10 min.), the temperature was fixed at 37° C. The heating process between both steps took around 20 seconds. The results are shown in Table 2 and in FIG. 1, where they are expressed as elastic modulus G' and loss tangent tan δ=G"/G', the ratio of elastic and viscous properties showing which one is the dominant one. When the tan δ value is 1, the elastic and viscous properties of the material are equal. The smaller the loss tangent, the more elastic is the material. For physical gels, the values are G'>G" and tan δ<1. For viscous liquids, the values are G">G' and tan δ>1. For the data in Table 2 and FIG. 1, the formulations tested were prepared using the recipes in Tables A and D for 165.5 and 165 g total, respectively.

TABLE 2

Results of Rheological Tests for Polymer Composite Formulations Before and After Sterilization. Values for G' and tan δ were recorded 10 min after application of stress. Angular frequency f = 0.1 Hz, oscillatory stress τ = 1 Pa.

| Formulation | Conditions | T = 25° C. | | T = 37° C. | |
| --- | --- | --- | --- | --- | --- |
| | | G' (Pa) | tan δ | G' (Pa) | tan δ |
| F1-20141210 | Before sterilization | 17 | 0.83 | 560 | 0.07 |
| | After sterilization | 8.7 | 0.91 | 650 | 0.05 |
| F4-20141210 | Before sterilization | 480 | 0.15 | 9800 | 0.03 |
| | After sterilization | 440 | 0.10 | 5500 | 0.05 |

Figure 1B:
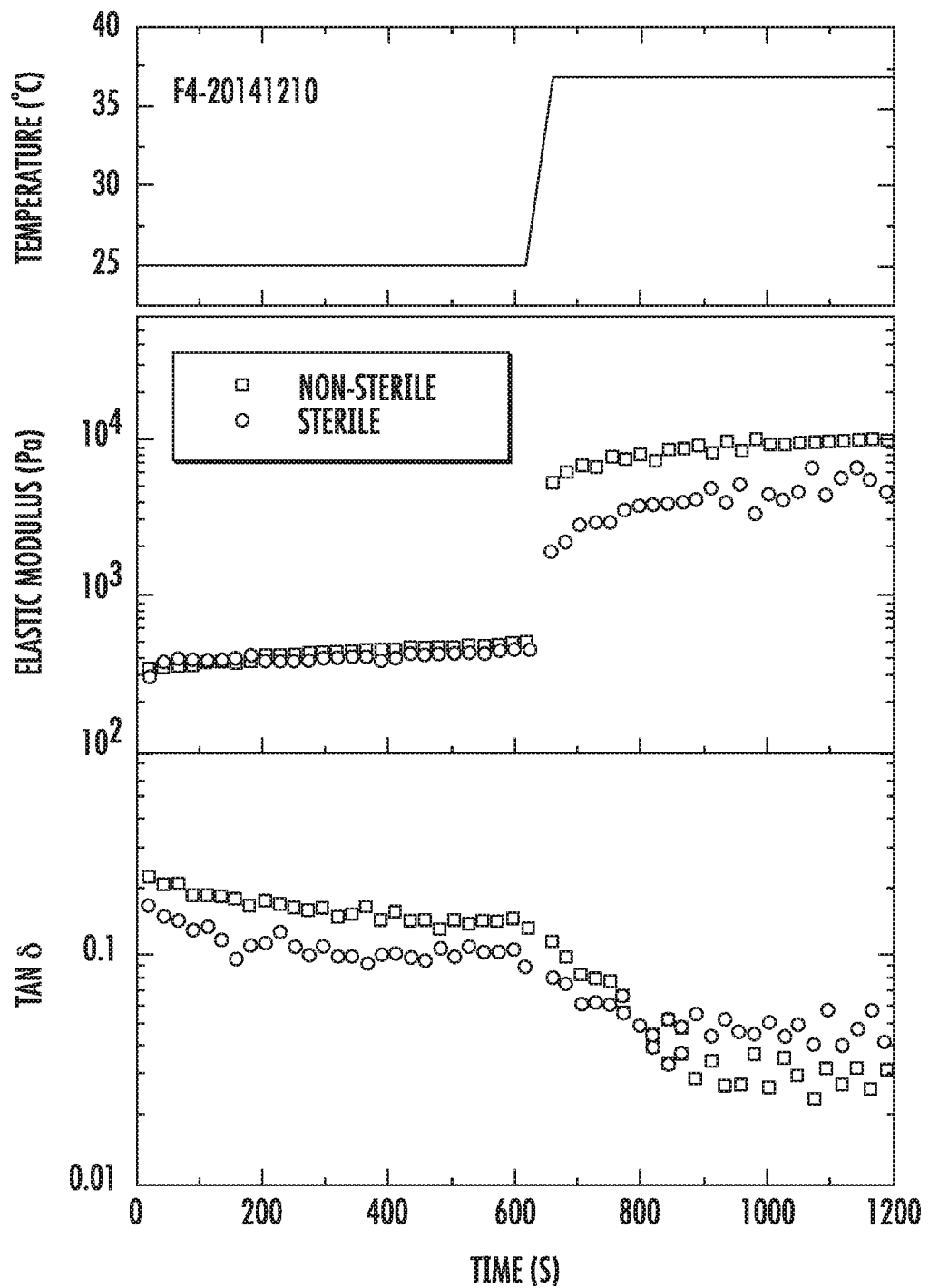
FIG. 1B shows graphs of time dependence of elastic modulus (G') and loss tangent (tan $\delta$=G"/G') upon a temperature jump from 25 to 37° C. recorded at f=0.1 Hz and oscillatory stress of $\tau$=1 Pa, for the F4-20141210 formulation.

Sterile formulations were characterized by slightly smaller value of elastic modulus compared to their non-sterile counterparts. This difference was however small, especially in the case of F4-20141210. At 37° C., elastic modulus increased significantly. This was accompanied by a fast decrease of loss tangent, indicating the reinforcement of the gel structure. This process took about 1-2 min. for the formulation F4-20141210 and it was slightly longer (about 5 min.) for the sample F1-20141210. Sterilization of the samples did not affect significantly the kinetics of the viscosity enhancement nor the final values of G' and tan δ reached by the samples at 37° C. (FIG. 1).

In conclusion, two composite gels were tested. The composites were infusible due to their shear-thinning properties. They showed temperature-induced thickening, i.e., their gel structure became stronger upon an increase of temperature. Although sterilization of the samples induced a few subtle changes in the appearance of the samples, the elasticity of the formulations, the extent of temperature-induced thickening, and the time-scale of this process are not affected significantly by the sterilization process.

Example 3

Further Studies on Sterilization of Polymer Composite Formulations

The F1 and F4 formulations are water-swellable polymer composites that undergo a rapid gelation upon increasing temperature, pH and/or ionic strength. The composites contain two hydrophilic polymers and ionic gelators. The first polymer undergoes temperature-induced gelation and enables formation of elastic gel at about 37° C. The second polymer forms a gel upon contact with ionic gelators introduced to the formulation. The strength of the gel of the second polymer depends on the amount of gelator added, as well as pH and ionic strength of the formulation (typically, pH of about 5.1 to 6.8 and ionic strength of about 5 g/L).

In Example 2, it was shown that flow properties of the formulations were not significantly affected by sterilization. This further study shows the effect of sterilization on the water-swellable polymer composites.

For the sample F1-20141210, rheological measurements were repeated twelve weeks following sterilization. During this period the sample was stored in the dark in closed plastic vials at room temperature. Visual observation confirmed that the appearance and consistency of the sample did not change significantly after 12 weeks of storage. In addition, no visual sign of microorganism growth was detected in the sample.

First, the changes in flow properties upon a jump in temperature from 25° C. to 37° C. were monitored. The values of elastic and storage moduli as a function of time at a constant stress (1 Pa) and frequency (f=0.1 Hz) were followed. In the first step of the experiment (10 min.), the temperature was kept at 25° C. In the second step (10 min.), the temperature was fixed at 37° C. The heating process between both steps took around 20 seconds. The results are shown in Table 3 and FIG. 2; they are expressed as elastic modulus G' and loss tangent tan δ=G"/G', the ratio of elastic and viscous properties showing which one is the dominant one. With a tan δ value of 1, the elastic and viscous properties of the material are equal. The smaller the loss tangent, the more elastic is the material. For physical gels, the values are G'>G" and tan δ<1. For viscous liquids, the values are G">G' and tan δ>1. For the data in Table 3 and FIG. 2, the formulations tested were prepared using the recipes in Tables A and D for 165.5 and 165 g total, respectively.

TABLE 3

Results of Rheological Tests for the F1-20141210 Formulation Immediately and 12 Weeks After Sterilization. Values for G' and tan δ were recorded 10 min after the application of the stress. Angular frequency f = 0.1 Hz, oscillatory stress τ = 1 Pa.

| Conditions | T = 25° C. | | T = 37° C. | |
| --- | --- | --- | --- | --- |
| | G' (Pa) | tan δ | G' (Pa) | tan δ |
| Immediately after sterilization | 8.7 | 0.91 | 650 | 0.05 |
| 12 weeks after sterilization | 10 | 1.3 | 420 | 0.05 |

Figure 2:
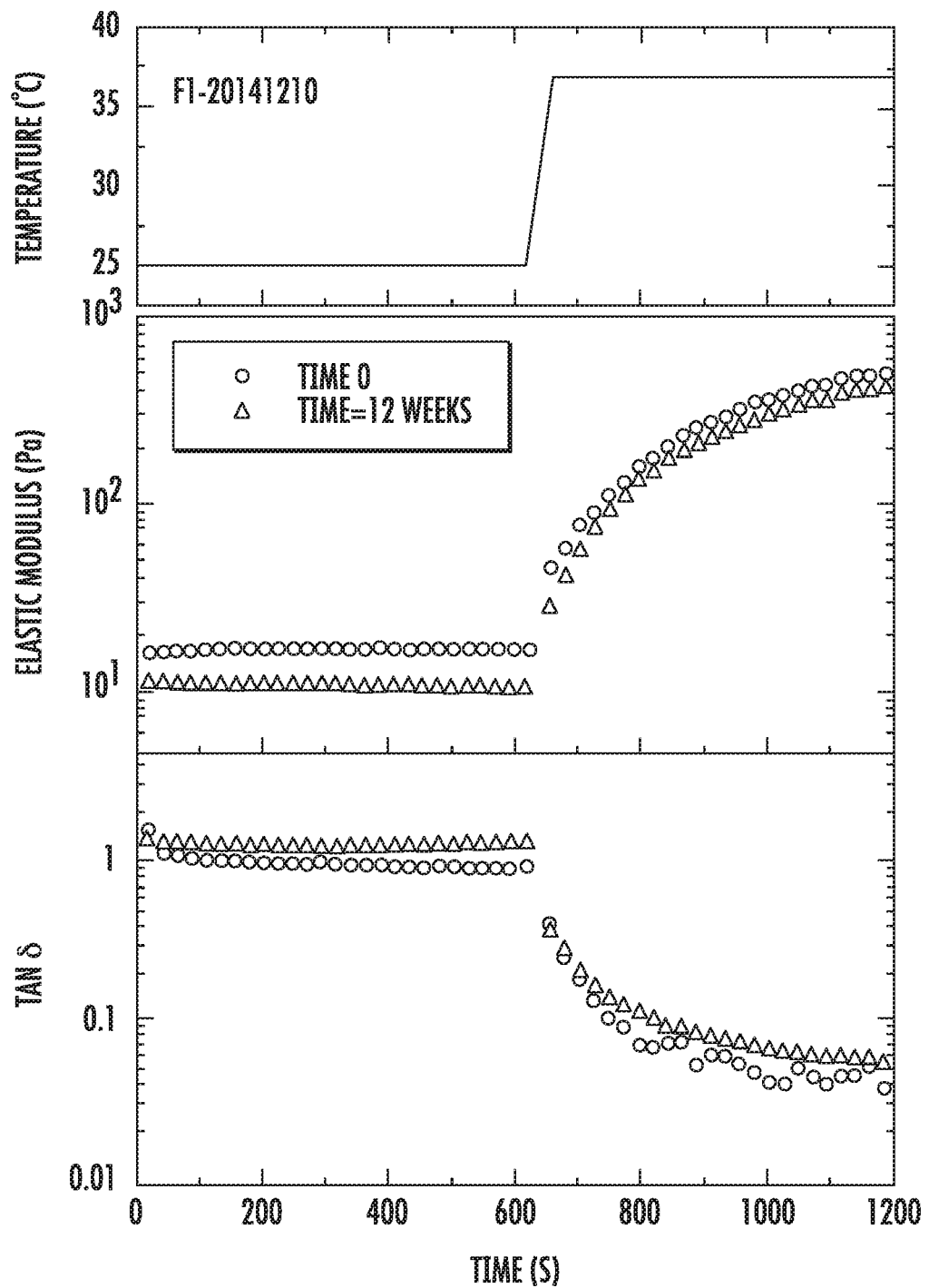
FIG. 2 shows a graph of time dependence of elastic modulus (G') and loss tangent (tan $\delta$=G"/G') upon a temperature jump from 25 to 37° C. for F1-20141210 formulation recorded at time 0 and 12 weeks after sterilization at f=0.1 Hz and oscillatory stress of $\tau$=1 Pa.

The data show that storing the F1-20141210 sample for 12 weeks did not affect significantly the flow properties or the extent of the thermothickening effect (FIG. 2). At 25° C., the sample showed loss tangent of about 1. Heating to 37° C. was accompanied by a fast decrease of tan δ, indicating the reinforcement of the gel structure. The kinetics of this process was similar for freshly sterilized and 12 week-old samples.

Figure 3:
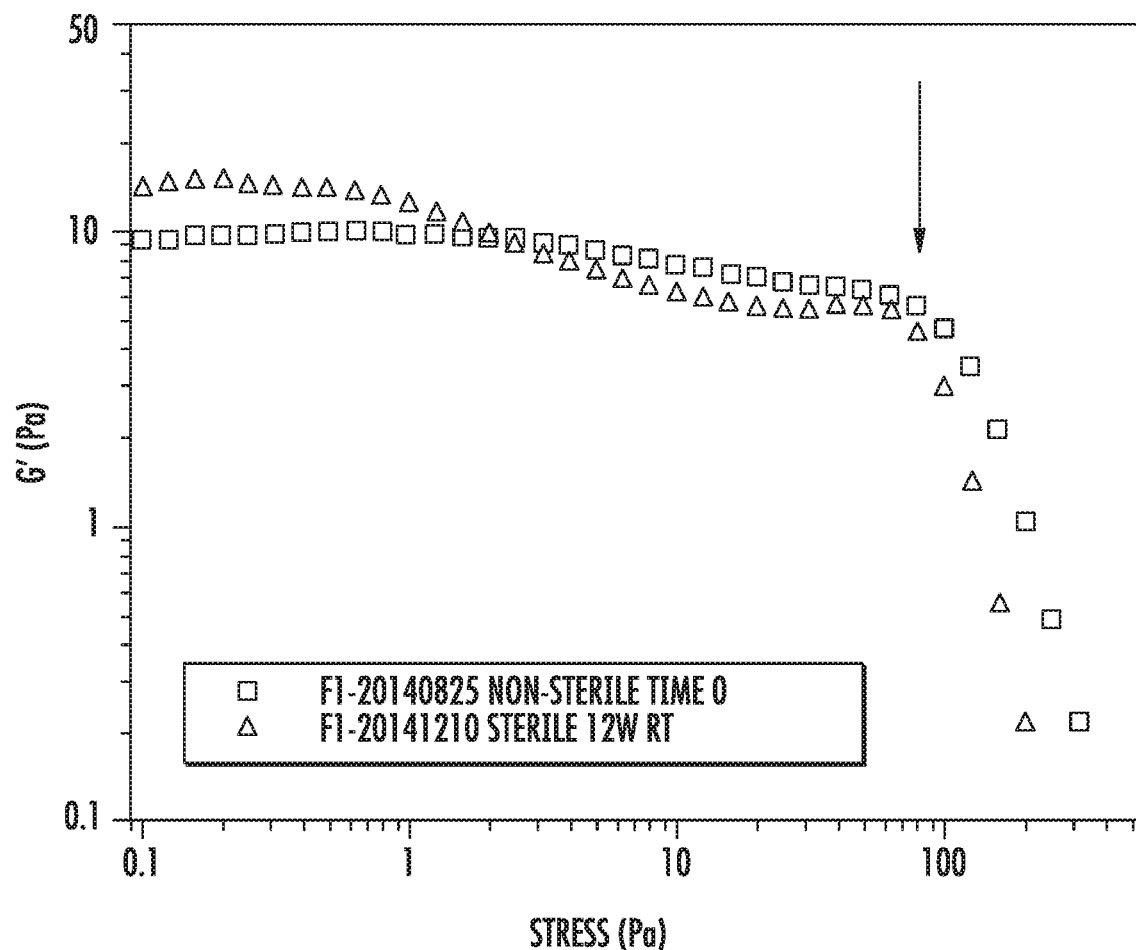
FIG. 3 shows a graph of stress sweep results for the formulations F1-20140825 (nonsterile) and F1-20141210 (sterile and stored for 12 weeks at room temperature) registered at oscillation frequency f=0.1 Hz and temperature T=25° C. The arrow indicates the onset of the shear-thinning region, which was similar for both samples.

A stress sweep test (i.e., measurements of elastic and loss moduli as a function of stress at a fixed frequency) was performed in order to confirm the shear-thinning character of the sample stored for a 12-week period. The results are shown in FIG. 3. At low applied stresses, the values of elastic modulus G' were constant and similar to those obtained for the F1-20140825 sample (prepared using the recipe in Table A for 110 g total) (i.e., non-sterile sample prepared under similar conditions to those for F1-20141210, which was prepared in a batch of 165.5 g total). Shear-thinning behavior (i.e., a decrease of elastic modulus G' as a function of applied stress) was observed for both formulations at a similar value of about 80 Pa. These results confirm that the syringeability of the sample will not be significantly affected upon 12-week storage at room temperature.

In conclusion, the physico-chemical stability of one of the composite gel samples was assessed after 12 weeks of storage at room temperature (in a closed container, in the dark). The results show that the flow properties and syringeability of the sample are not significantly affected after 12 weeks of storage time.

Example 4

Preparation of Pluronic® F127 Gel Reinforced with Nanocrystalline Cellulose

Development was performed in terms of (1) the onset of gelation of formulation at temperature close to body/skin temperature (32-35° C.), (2) syringeability of formulation at room temperature, and (3) time needed to induce the formation of the gel at 35° C.

All formulations were prepared using the following procedure: Pluronic® F127 polymer was molten in a 20 mL glass vial with heating and stirring (1.6 to 1.8 g). A filler (nanocrystalline cellulose (NCC)) was added, if required (100 or 200 mg). Stirring and heating were continued for about 5 min. Chitosan solution in 2% aq. AcOH was added under stirring to a final weight of the sample of 10 g. The sample was kept under vigorous stirring overnight (no heating).

The onset of gelation was measured by heating the sample in a water bath to the desired temperature. For several formulations, syringeability/ability to flow was verified at room temperature by passing about 3 mL of formulation from a 10 mL plastic syringe through a 16-gauge needle.

In a separate experiment, gelation time was estimated by depositing a drop of the sample kept at room temperature through a 16-gauge needle on the wall of a plastic Eppendorff tube heated to 37° C. The time needed to stop the flow of the solution was taken as an approximation of the gelation time.

Chitosan solutions were prepared as follows: A solution of chitosan (CH, 2% w/w) was prepared by overnight vigorous stirring of chitosan powder suspended in 2% AcOH, resulting in the formation of a transparent and homogeneous yellowish solution. This solution was diluted to a concentration of 1% and 0.5% with water followed by the addition of 0.5% NaOH solution to pH of about 6. Chitosan solutions are shown in Table 4.

(i.e., the samples become liquid upon cooling to temperatures lower than their gelation point as determined upon heating).

Example 5

Synthesis of Modified Chitosan Gel

Carboxymethyl chitosan was prepared as follows: Carboxymethylation was carried out by stirring chitosan (2 g) in 20% NaOH (w/v 100 mL) for 15 min. Monochloroacetic acid (15 g) was then added dropwise to the reaction mixture and the reaction was continued for 2 hours at 40+/−2° C. with stirring. The reaction mixture was then neutralized with 10% acetic acid, and then poured into an excess of 70% methanol. The carboxymethyl chitosan produced was filtered using a G2 sintered funnel and washed with methanol. The product was dried in a vacuum at 55° C. for 8 hours to give 6.5 g of dried carboxymethyl chitosan. The degree of substitution of carboxymethyl chitosan (CMCh) was determined to be 0.75 using methods as described (Biomacromolecules, Vol. 5, no. 2, 2004).

Polyvinyl acetate (PVA) (1 g) was dissolved in water (85 mL) at 45° C. After the PVA-water solution cooled to room temperature, acetone (15 mL) was added dropwise to the vigorously stirred PVA solution for 15 min to form about a 1% (w/v) PVA solution. Then the solution was kept at 5° C. for 24 hours until it became light yellow, which indicated that the long chains of PVA had shrunk to nanoparticles. Different amounts of CMCh (0.5, 1 and 2 wt %) were then added to the solution. The solution was purged with $N_2$ for

TABLE 4

Chitosan Solutions

| Pluronic® F127 final concentration (wt %) | Solvent | Additive | Gelation temperature | Injectability at room temperature |
|---|---|---|---|---|
| 16% | aq. AcOH (2%) | N/A | >40° C. | + |
|  | 1% CH in AcOH | N/A | >40° C. | + |
|  | 2% CH in AcOH | N/A | 38° C. | + |
| 17% | aq. AcOH (2%) | N/A | 37° C. | + |
|  | 1% CH in AcOH | N/A | 37° C. | + |
|  | 2% CH in AcOH | N/A | 37° C. | + |
| 18% | 0.5% CH in AcOH | N/A | 32° C. | + |
|  | 1% CH in AcOH | N/A | 31° C. | +* |
|  | 2% CH in AcOH | N/A | 31° C. | +* |
| 18% | 1% CH in AcOH | NCC 100 mg | 29° C. | + |
| 17% | 1% CH in AcOH | NCC 100 mg | 36° C. | + |
|  |  | NCC 200 mg | 34° C. | + |
|  |  | NCC 500 mg | 29° C. | + |

*For these samples, gelation time was estimated; the droplet of formulation formed a gel almost immediately after contact with the wall of the Eppendorf tube.

Figure 4:
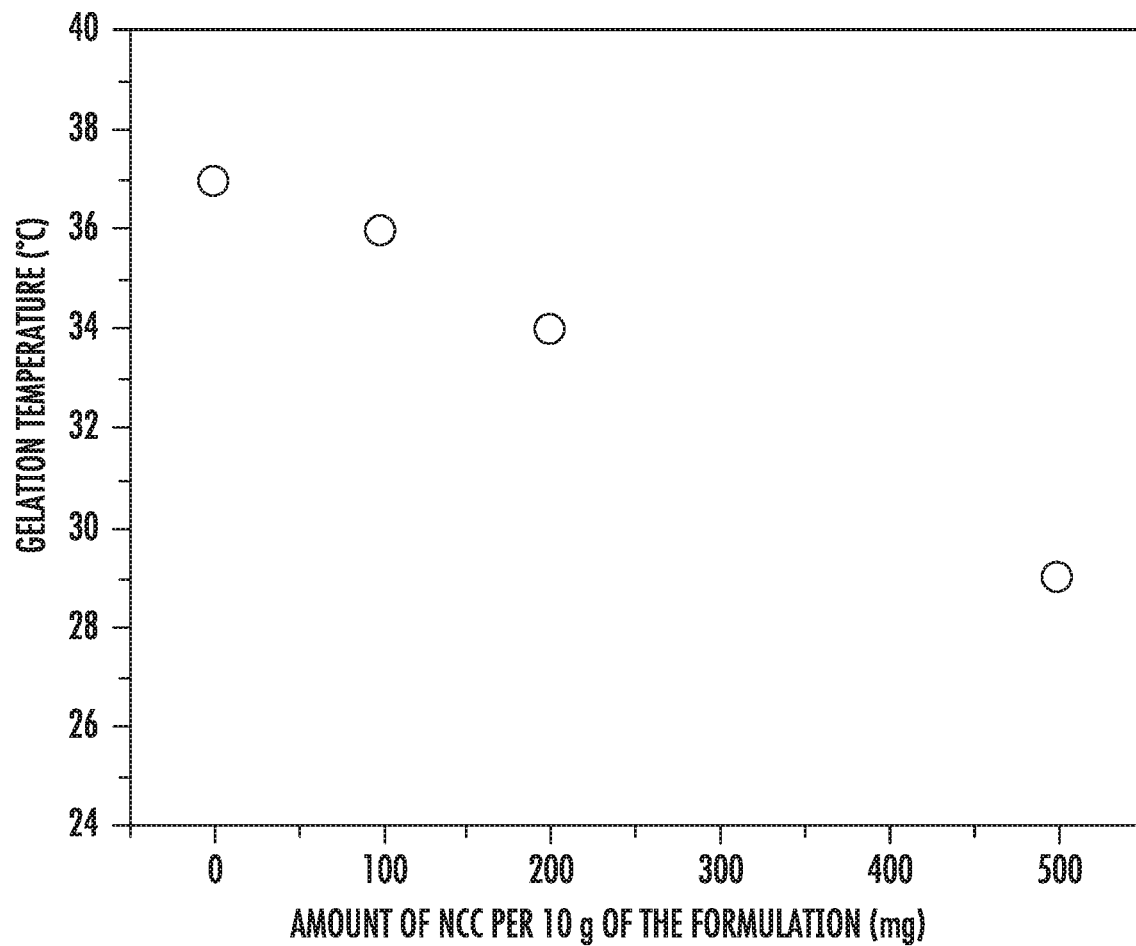
FIG. 4 shows a graph of dependence of the gelation temperature on the amount of nanocrystalline cellulose (NCC) for a formulation of 17% w/w Pluronic® F127 in 1% w/w chitosan (CH) (pH of around 6).

A graph showing dependence of the gelation temperature on the amount of nanocrystalline cellulose (NCC) for the formulation of 17% Pluronic® F127 in 1% CH (pH at about 6) is shown in FIG. 4.

Gelation temperature of the formulations could be adjusted by adjusting the concentration of Pluronic® F127. The presence of CH had no effect on gelation. All samples were syringeable at room temperature. For formulations having 18% Pluronic® F127 in 1% or 2% CH solution, the gelation time was estimated to be almost immediate. Addition of NCC led to a decrease in gelation temperature. NCC strengthened the gels and induced temperature hysteresis 30 min, then 4.0 mmol methylenebisacrylamide (MBA), 0.4 mmol potassium persulfate (KPS), and 0.67 mmol tetramethylenediamine (TEMED) were added to the solution, and polymerization was carried out for 15 hours at 30° C. The nanogels formed were either used directly or could be frozen to form a freeze-dried powder which is easily pre-dispersed in water, forming nanoparticle dispersion, before use.

Acyl chitosan was prepared as follows: $MeSO_3H$ was used as a solvent for chitosan in order to help protect the amino groups on the chitosan molecules from acylation reaction. Typically, chitosan was dissolved in $MeSO_3H$ at room temperature for 1 hour and octanoyl chloride was then added dropwise under stirring, with the molar ratio of octanoyl chloride to the repeating unit of chitosan being equal to 0.66:1. The reaction was allowed to continue for 5 hours at ambient temperature before it was stopped by the addition of crushed ice. The resulting solution was dialyzed for one day to remove most of the acid, and the remaining acid and ammonium salt were subsequently neutralized with NaHCO$_3$. The final mixture was dialyzed against Milli-Q water for more than 3 days and then lyophilized as acyl chitosan (AC) powder.

Example 6

Synthesis of PVA-Acylate

Materials: Polyvinyl alcohol (PVA), 186K, 87%-89% hydrolyzed: 10 g. R—COCl (e.g., lauroyl chloride, palmitoyl chloride, octanoyl chloride): 1.68 g. Triethylamine (ET$_3$N): 2.25 mL. 1-methyl-2-pyrrolidone (NMP): 100 g.

In alternate experiments, the materials were as follows: 10 g PVA, 186 K, 87-89% hydrolyzed; 3.36 g R—COCl (lauroyl chloride, palmitoyl chloride, or octanoyl chloride); 4.50 mL ET$_3$N; and 150 mL NMP.

Synthesis Procedure: PVA was added to hot NMP; if too viscous, then more NMP was added, up to a final volume of 50 mL. After complete dissolution, the R—COCl was added, followed by the ET$_3$N. The mixture was left at room temperature overnight with stirring. The PVA-acylate was then diluted by adding 3 times water, stirring, and then purified through dialysis over 5 days, and then lyophilized. Yield: 90%.

Figure 5:
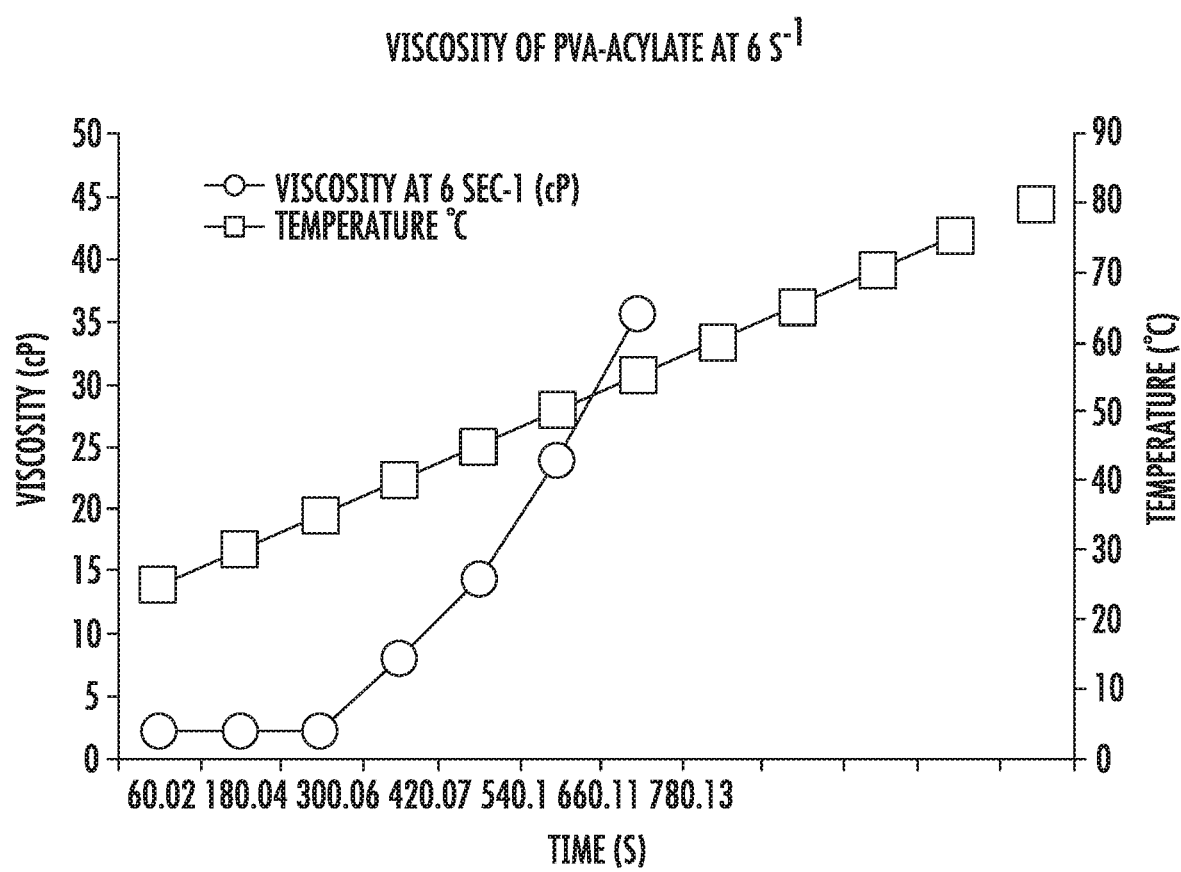
FIG. 5 shows a graph of viscosity of PVA-acylate at 6 s$^{-1}$ as a function of time and at different temperatures.

Viscosity at 6 s$^{-1}$ of PVA-acylate thus prepared is shown in FIG. 5.

Example 7

Evaluation of Retention and Tolerance of Teat Sealants Infused in Cows

The objective of this study was to evaluate the retention and the toleration of the novel use of two sol-gel polymer composite formulations (F1 and F4, prepared using the formulations in Tables A and D, respectively, for 165.0 g total) as intramammary teat sealants (ITS) during the dry period of dairy cows.

Eight cows (adult lactating pregnant Holstein dairy cattle) were dried off at initiation of study and each quarter was assigned one of two treatment groups, T01 and T02. Group T01 received treatment with F1 while Group T02 received treatment with F4. Spectramast® DC (ceftiofur hydrochloride) dry cow therapy was administered per quarter per label instructions prior to sealant infusion. Formulations were steam sterilized prior to infusion. All doses of the ITS were administered as intramammary infusions to all available quarters of an assigned cow. All eight animals were allotted for consistent ultrasound evaluation at defined times throughout the duration of the study. Approximately 60 days after administration, upon calving, all test ITS was removed by hand stripping. General health observations and visual udder/quarter observations were performed and recorded throughout the study.

The ITS formulations were delivered via either a syringe and specialized mixing tip attachment or ready-to-use plastets, intramammary (IMAM), 2.0 mL. The partial insertion method of administration was used. F1 and F4 were infused at 2.2 g+/−0.5 g. Both formulations were easily infused although an initial resistance to initiate was noticed due to the shear thinning properties of the substrate. The F4 required more force to infuse as compared to the F1. However, once flow was initiated, the F4 became easier to infuse. All syringes had been autoclaved prior to infusion. Infusion of the substrate into all test teats in animals was easily accomplished. No syringes demonstrated defects. No syringes demonstrated difficulty for infusion.

Calves were understood to be removed immediately at birth, and therefore not allowed to suckle. Substrate was easily removed via manual stripping from all teats at the first milking of the animal post-calving, approximately 60 days after administration. No difficulty was indicated upon removal of any of the substrate from the teats of any animals.

Samples of the first milk post-calving were collected to analyze for presence of sealant substrate. Sample weights post removals were not determined due to the inability to distinguish teat sealant material from colostrum. As a consequence of the teat sealants' properties of being shear-thinning and temperature sensitive and because shear force was exerted on the formulations to remove them from the teat cistern, the formulation had thinned upon removal from the teat. Additionally, since these formulations gel at warmer temperatures and become liquid at colder temperatures, placing the colostrum stripping samples collected into the refrigerator immediately post-collection further thinned the formulation. When the formulation returned to liquid form in the cold temperature of the refrigerator, it became difficult by conventional means to separate the sealant substrate from the colostrum to facilitate accurate percent recovery for a measurement of total substrate removed.

A pathologist examined the interior of the teat canals for safety of formulations. No gross lesions were identified that had any relevance to the test substrate or formulations. One incidence of one teat having a mild subepithelial fibrosis and mononuclear infiltration was noted. This finding could not be correlated to test substrate. All other teats examined were normal with no adverse findings. Tissues were sent for sectioning if any areas of gross pathologic concern were identified to rule out any substrate concerns but none were identified. Microscopic tissue assessment from this retention study resulted in no substrate-related findings.

The formulations had remained in the teats until calving, and were visually assessed throughout the retention period via ultrasound scoring. Ultrasound observations were performed by trained staff to assess presence of sealant on days 0, 1, 4 then weekly thereafter until calving. Numbers were logged on a visual scale from 0 (no sealant evident in teat cistern) to 5 (teat cistern appears fully blocked with sealant). Any unusual observations were recorded on the daily observations form. All formulations stayed in the teats throughout the dry cow period without incidence.

The results of the ultrasound scoring are shown in the below Tables 5 and 6 for F1 and F2, respectively:

TABLE 5

F1 Formulation Ultrasound Scoring

| Cow ID | Quarter | Day 0 | Day 1 | Day 4 | Day 7 | Day14 | Day 20 | Day 28 | Day 47 |
|---|---|---|---|---|---|---|---|---|---|
| 556 | LF | 5 | 4.5 | 5 | 5 | 5 | 3.5 | 4 | 4 |
| 556 | RR | 5 | 5 | 5 | 4.5 | 5 | 4.5 | 3.5 | 3.5 |
| 557 | LF | 5 | 4 | 4.5 | 4 | 4 | 3.5 | 4 | 4 |
| 557 | LR | 4.5 | 4 | 4 | 4 | 4.5 | 3.5 | 3.5 | 4 |
| 558 | LF | 5 | 4 | 5 | 4.5 | 4 | 4 | 4 | 4 |
| 558 | RF | 5 | 4 | 5 | 4 | 4.5 | 3.5 | 3.5 | 4 |
| 559 | LF | 4.5 | 4 | 4 | 4 | 4 | 4 | 3.5 | 4 |
| 559 | LR | 5 | N/A | 5 | 5 | 4 | 4 | 3.5 | 3.5 |
| 560 | LR | 4.5 | 4 | 4 | 4 | 4 | 4 | 4 | 3.5 |
| 560 | RF | 5 | 4 | 4 | 4 | 4 | 4 | 4 | 4 |
| 561 | LR | 5 | 4 | 3 | 3.5 | 5 | 3 | 3.5 | 3.5 |
| 561 | RF | 5 | 3 | 5 | 5 | 5 | 3.5 | 3.5 | 3 |
| 562 | LR | 4.5 | 4 | 3.5 | 3.5 | 3.5 | 3 | 3 | 3 |
| 562 | RR | 5 | 4 | 3 | 5 | 3.5 | 3.5 | 3.5 | 3.5 |
| 563 | LR | 5 | 5 | 4 | 3 | 4 | 4 | 4 | no video |
| 563 | RR | 5 | 5 | 4 | 3 | 4 | 4 | 4 | no video |

TABLE 6

F4 Formulation Ultrasound Scoring

| Cow ID | Quarter | Day 0 | Day 1 | Day 4 | Day 7 | Day 14 | Day 20 | Day 28 | Day 47 |
|---|---|---|---|---|---|---|---|---|---|
| 556 | LR | 5 | 4 | 4.5 | 4 | 4.5 | 4 | 4 | 3.5 |
| 556 | RF | 4.5 | 4 | 4.5 | 4 | 4.5 | 4.5 | 4 | 4 |
| 557 | RF | 4 | 4 | 4 | 4 | N/A | 4 | 3.5 | 4 |
| 557 | RR | 5 | 4 | 4 | 4 | 4 | 4 | 3.5 | 4 |
| 558 | LR | 5 | 5 | 4 | 5 | 4.5 | 3 | 3 | 4 |
| 558 | RR | 4.5 | 3.5 | 4 | 2.5 | 3.5 | 3.5 | 3.5 | 3.5 |
| 559 | RF | 4.5 | N/A | 4 | 4 | 4 | 4 | 3 | 3.5 |
| 559 | RR | 4.5 | 4 | 4 | 5 | 4 | 3.5 | 3 | 3.5 |
| 560 | LF | 4 | 4 | 4 | 3 | 3.5 | 3.5 | 3 | 4 |
| 560 | RR | 5 | 3.5 | 4 | 3 | 3 | 4 | 3 | 4 |
| 561 | LF | 5 | 4 | 5 | 5 | 5 | 3.5 | 3.5 | 3 |
| 561 | RR | 5 | 3 | 4 | N/A | 3.5 | 3.5 | 3 | 3.5 |
| 562 | LF | 4.5 | 4 | 5 | 4 | 3.5 | 3.5 | 3 | 4 |
| 562 | RF | 5 | 4 | 5 | 4 | 4 | 4 | 4 | 4 |
| 563 | LF | 4.5 | 5 | 4 | 4 | 3.5 | 4 | 4.5 | no video |
| 563 | RF | 4.5 | 5 | 5 | 5 | 4.5 | 4.5 | 4.5 | no video |

In sum, the study showed that the sol-gel polymer composite formulations were easy to administer by intramammary infusions and to remove by manual stripping. The results also indicated that the dairy cows tolerated the teat sealants without adverse side effects. Finally, the results demonstrated retention of the teat sealants during the dry period of dairy cows until the sealants were physically removed at the end of the study.

Example 8

Evaluation of Retention and Tolerance of Teat Sealants Infused in Cows

The objective of this study was to evaluate the retention and the toleration of the novel use of two sol-gel polymer composite formulations (F1 and F4, prepared using the formulations in Tables A and D, respectively, for 165.0 g total) as intramammary teat sealants (ITS) during the dry period of dairy cows.

Thirty cows (adult lactating pregnant Holstein dairy cattle) were dried off at initiation of study and each quarter was assigned one of four treatment groups, T01 to T04. Two dose volumes of 2.0 and 3.0 mL per formulation were infused to evaluate if volume had an effect on retention. Groups T01 and T02 received treatment with F1 at a volume of about 2.0 mL (actual delivered: average 1.99+/−0.19) and about 3.0 mL (actual delivered: average 2.88+/−0.15), respectively. Groups T03 and T04 received treatment with F4 at a volume of about 2.0 mL (actual delivered: average 1.54+/−0.37) and about 3.0 mL (actual delivered: average 2.24+/−0.55), respectively. Animals were first acclimated to the facilities, diet and water source for at least 10 days prior to initiation of study. On study day −1+/−2 days, prior to morning milking, milk quarter samples were taken for somatic cell count analysis and bacterial assessment.

Spectramast® DC (ceftiofur hydrochloride) dry cow therapy was administered per quarter per label instructions prior to sealant infusion. All doses of ITS were administered as intramammary infusion to all available quarters of an assigned cow. Weekly ultrasound evaluation of the teats of all thirty animals at defined times throughout the study were completed in an effort to determine retention and evaluation of the sealants as a physical barrier.

The teat ends of all four quarters of fifteen animals were exposed weekly to a bacterial suspension throughout the dry period and after administration of teat sealant and dry cow therapy to simulate poor hygienic conditions in the dairy. A frozen stock of *E. coli* was used to prepare the bacterial suspension of $1 \times 10^6$ colony forming units/mL (CFU/mL) in Trypticase Soy Broth. All four teat ends of the animals were exposed to the *E. coli* preparation via a single dip from a dip cup once weekly starting on day 7. Exposure to *E. coli* ceased post-calving or removal of teat sealant.

Approximately 60 days after administration and at the first milking post-calving, test ITS was removed by hand stripping. Recovered sealant samples were stored at room temperature. Beginning on the day of first milking post-calving, each cow was observed for clinical signs of mastitis. Sterile quarter samples for bacteriological culture were collected from each udder quarter after careful cleaning and pre-stripping of each individual teat on day 1, 2, 3, 7, 10 and 14 post-calving. Milk and colostrum samples were collected at various times throughout the experiment in order to measure potential residues or metabolites. Somatic cell counts and milk weight were also recorded to assess udder condition, presence of mastitis and quality of milk.

Ultrasound analysis for all substrates indicated the presence of a significant amount of material throughout the dry period irrespective of the dose volume. Substrate was observed to undergo changes in appearance between days 14-35. Both formulations appeared to persist in the teat canal and remained as a protective barrier throughout the dry period until physical removal of the teat sealants. Post-calving substrate was removed from the teat through manual stripping.

Upon return to lactation, udder health, milk appearance and bacterial presence were monitored over a two week period for all animals remaining in the study. While abnormal (elevated) udder health scores were noted in a small number of individual cows for all treatment groups over the course of the 14-day period, these could not be attributed to teat sealant failure. Neither udder health or milk quality scores were statistically different between treatment groups.

Properly designed and monitored field studies will be needed to confirm prevention of mastitis. However, based on this retention study, it can be concluded that the sol-gel polymer composite provides a sufficient, long-lasting physical barrier that is able to protect healthy dairy animals from new infections or re-infections.

In summary, all treatments remained throughout the dry period and appeared to protect the teat through ultrasound evaluation. All substrates were easily removable and no treatment related effects were noted upon gross and microscopic evaluation of tissues. Overall, both formulations F1 and F4 performed well with good retention throughout the dry period.

Example 9

Evaluation of Use of Sol-Gel Polymer Composite for Drug Release

The objective of this study was to evaluate the release and the antimicrobial activity of an antibacterial agent via the sol-gel polymer composite formulation. Formulation F2, prepared as described hereinabove, was used and loaded with 20 mg of amoxicillin per gram of formulation without affecting its rheological property which by extension is related to plug formation for teat sealing.

Amoxicillin Loading:

A loaded F2 sol-gel polymer composite formulation was prepared by thoroughly mixing methylcellulose (8.0 m %), chitosan (2.0 m %), amoxicillin trihydrate (2.0 m %), and monopotassium phosphate (0.76 m %) into 0.1 M acetic acid until an homogenous off-white cream was obtained.

The rheological data of the loaded F2 sol-gel was compared with that of the unloaded F2 sol-gel polymer composite (Table 7). The data from Table 7 represent the average properties of several batches (from the same raw materials) of either unloaded (n=6) or loaded (n=3) sol-gels. The shear storage modulus G' and the shear loss modulus G" values were statistically equal between the two sol-gel formulations; the tan δ values were thus trivially also equal. This demonstrates that these relevant physical properties of the sol-gel polymer composite were unaffected by the incorporation of 2 m % amoxicillin.

Amoxicillin Quantification:

In order to monitor amoxicillin release from the loaded sol-gel polymer composite, a simple spectrophotometric method was employed to quantify the drug. Absorbance at 274 nm has been correlated to amoxicillin concentration in phosphate aqueous buffer using $\varepsilon_{274}=1.2$ mM$^{-1}$ cm$^{-1}$ (Cary 60 UV-V is spectrophotometer, Agilent Technologies). This extinction coefficient is consistent with other values found in the literature ($\varepsilon_{274,\ ethanol}=1.4$ mM$^{-1}$ cm$^{-1}$ and $\varepsilon_{272,\ HCl\ 0.1M}=1.1$ mM$^{-1}$cm$^{-1}$; *The Merck Index Online*).

Amoxicillin Release.

Figure 8:
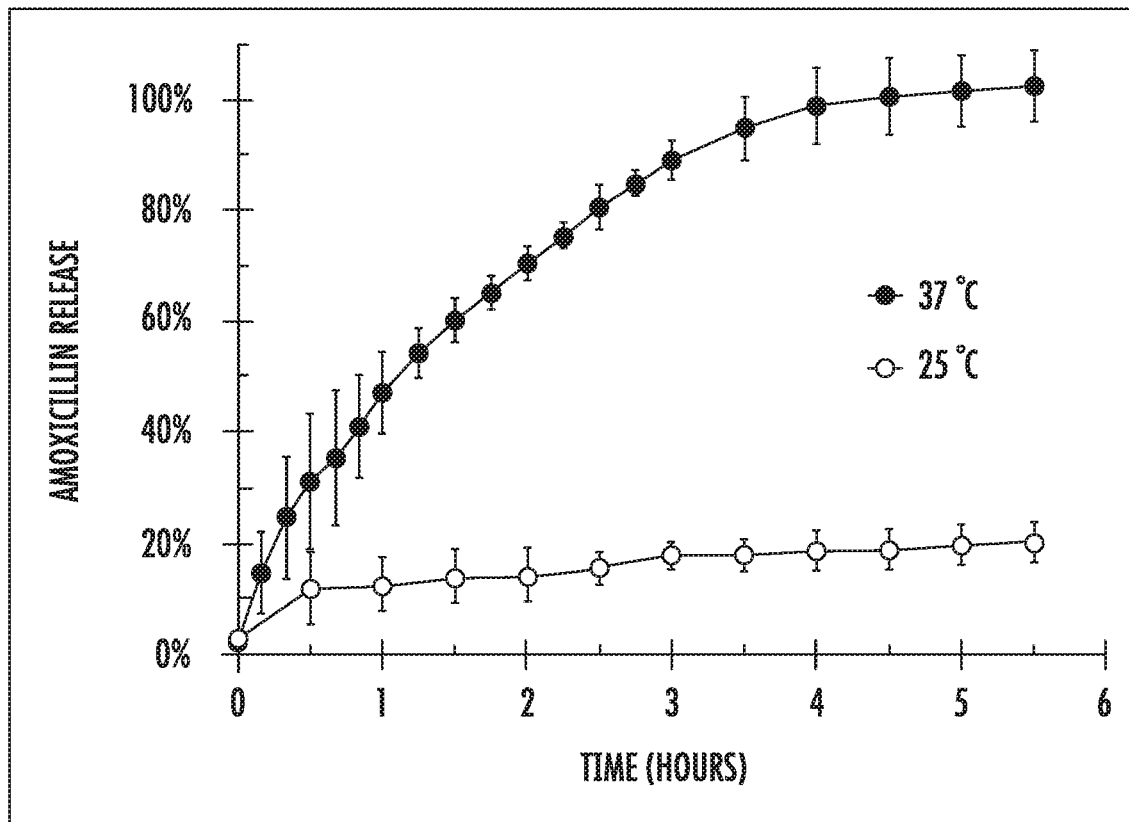
FIG. 8 shows the average release rate of amoxicillin from sol-gel polymer composite formulation F2 at T=25° C. and T=37° C. Error bars represent standard deviation (n=3).

An amount of loaded sol-gel polymer composite was first deposited at the very bottom of a quartz cuvette, held at either T=37° C. or T=25° C. The cuvette was then filled with a known volume of phosphate buffer (100 mM KH$_2$PO4, 100 mM NaCl, pH=6.5). At this point, amoxicillin started diffusing out of the sol-gel. This release was monitored by following the absorbance of the solution above the sol-gel aliquot at 274 nm. Amoxicillin release (FIG. 8) was calculated by $$\text{Release }\%=(A/\varepsilon l)\cdot(n_{amox}/V)$$

where A is absorbance at 274 nm, ε is the extinction coefficient of amoxicillin at 274 nm (1.2 mM$^{-1}$cm$^{-1}$) l is the path length of the cuvette, $n_{amox}$ is the quantity of amoxicillin initially contained in the sol-gel deposited to the cuvette bottom, and V is the total volume in the cuvette (i.e., $V_{buffer}+V_{gel}$). The curves on FIG. 8 represent the average release from experiments performed on 3 sol-gel polymer composite batches. The 37° C. curve (that is, physiological temperature) depicted an early release behavior by the sol-gel, with 50% of the drug released over about 1 hour, followed by a sustained release until 100% of amoxicillin was released after approximately 6 hours, which would be beneficial to achieving quick and sustained blood levels of the antimicrobial agent. At 25° C., the release was much slower, as only about 20% of amoxicillin was released of the sol-gel polymer composite after 5 hours. These results demonstrate that the loaded sol-gel formulation released its content following a fairly gradual release curve at physiological temperature. Furthermore, the release rate was found to be positively correlated to the sample temperature.

TABLE 7

Comparison of the rheological properties of the loaded and the unloaded sol-gels.

|  | T (° C.) | G' (Pa) | G" (Pa) | tan δ |
|---|---|---|---|---|
| Unloaded (n = 6) | 25 | 70 ± 40 | 30 ± 10 | 0.40 ± 0.10 |
|  | 37 | 700 ± 200 | 50 ± 10 | 0.07 ± 0.02 |
| Loaded (n = 3) | 25 | 80 ± 50 | 30 ± 10 | 0.37 ± 0.03 |
|  | 37 | 500 ± 100 | 40 ± 10 | 0.09 ± 0.04 |

Antimicrobial Activity:

The antimicrobial activity of the amoxicillin loaded sol-gel polymer composite was evaluated by the Kirby-Bauer Disc Susceptibility Test. Its inhibition zone was evaluated and compared with that of the non-loaded gel.

An aliquot of 1 g of amoxicillin loaded F2 sol-gel, prepared as described above, was spread on a 25 mm cellulose disc (Millipore). The disc was then deposited on a TSA II blood agar plate (Oxoid) that was inoculated with 100 μL of *Escherichia coli* ATCC 25922 in broth culture and diluted to match a 0.5 McFarland turbidity standard. The same procedure was used for the control experiment, which was carried out using a non-loaded F2 sol-gel.

After 24 hours of incubation, an inhibition zone of d=42 mm (Table 8) was visible in the surroundings of the cellulose disc for the loaded gel, while the control exhibited no inhibition zone. With an inhibition zone of 16 mm above disc size, the efficient antimicrobial action of amoxicillin on *E. coli* ATCC 25922 is observed.

TABLE 8

Summary Kirby-Bauer Disk Susceptibility Test results.

|  | T (°C.) | Inhibition zone (mm) |
|---|---|---|
| Unloaded (n = 1) | 37 | 0 ± 0 |
| Loaded (n = 3) | 37 | 42 ± 2 |

In summary, amoxicillin was shown by spectrophotometry to be entirely released from the sol-gel polymer composite within 6 hours at 37° C. while solely 25% was released at 25° C. Finally, the sol-gel polymer composite loaded with amoxicillin demonstrated a clear antimicrobial activity compared to unloaded sol-gel as evaluated by Kirby-Bauer's susceptibility disc method.

Example 10

Evaluation of Sol-Gel Polymer Composite as Barrier to Bacterial Migration

The purpose of the two tests in this study was to illustrate the ability of the sol-gel polymer composite formulations to act as a barrier against bacterial migration in a simulated glass cow teat.

The sol-gel polymer composite formulations F1-F4 shown in Table 9 were prepared as described hereinabove.

TABLE 9

Sol-gel polymer composite compositions.

| Sample | Chitosan | Methyl | Salt |
|---|---|---|---|
| F1 | 1.8% | 7.3% | sodium pyrophosphate tetrabasic 0.05% |
| F2 | 2% | 4% | potassium phosphate dibasic 0.7% |
| F3 | 2% | 4% | sodium pyrophosphate tetrabasic 0.025%/ potassium phosphate dibasic 0.35% |
| F4 | 1.8% | 7.3% | β-glycerophosphate disodium salt hydrate 3.6% |

The different sol-gel formulations can be defined by their respective rheological properties in the form of Tan δ, G' and G" as presented in Table 10.

TABLE 10

Rheological properties, pH and appearance of sol-gel polymer composite.

| Sample | Tan δ 25/37° C. | G' (Pa) | G" (Pa) | pH | Appearance |
|---|---|---|---|---|---|
| F1 | 1.59/0.04 | 4/672 | 7/23 | 6 | Tan liquid |
| F2 | 0.19/0.04 | 283/5798 | 52/239 | 6.59 | Tan, off-white |
| F3 | 0.65/0.04 | 24/2742 | 16/75 | 6.29 | Tan, off-white |
| F4 | 0.1/0.04 | 398/5315 | 38/200 | 6.75 | Yellowish, gel |

In addition, a control motility test medium labeled "BAM 103" was prepared by mixing tryptose 10.0 g/L and sodium chloride 5.0 g/L, then hardened by the addition of agar 5.0 g/L.

Test 1—Evaluation of Impermeability of Sol-Gel Polymer Composite to Bacteria:

Test 1 was based upon the standard bacteria motility test to test the ability of bacteria to migrate through a gel medium comprising the sol-gel polymer composite samples. For this purpose, the motile bacteria *Escherichia coli* ATCC 25922 was inoculated as a 1/10 dilution of overnight culture in Tryptic Soy Broth (TSB) to match a 0.5 McFarland turbidity standard. In a 15 mL polypropylene test tube, a 10 mL gel plug being investigated was first added, then a layer of Triphenyltetrazolium chloride (TTC 0.5 g/L) was added on top of each test formulation. TTC is a bacteria-sensitive dye, which forms a red precipitate upon reduction in contact with bacteria.

The bacterial solution cultured overnight in TSB was added as a third layer. 1 mL of this inoculum was added to the TTC and the test tube was incubated for 24 and 48 hours at 37° C.

The ability of the bacteria to migrate in the sol-gel polymer composite formulation is evaluated by the depth of red color measured from top to bottom of the lower sol-gel layer in the test tube. The test tubes were examined for color, which may spread from top to bottom depending on potential bacterial migration. There was an initial red color that appeared at the bacterial-gel interface due to partial penetration in the medium (reduction of TTC). As presented in Table 11, the F1-F4 sol-gel polymer composite formulations of the present disclosure do not allow bacterial penetration while BAM103 control allowed bacterial penetration within 48 h. Bacterial penetration of the stiff agar control was observed only at the interface between the F1-F4 gels and tubes, where the thin interfacial water layer of the agar formed.

TABLE 11

Results of measured bacterial penetration (n = 3) into different sol-gel polymer composite formulations and controls.

| Sample | Depth of bacterial penetration (mm) | |
|---|---|---|
| time | 24 h incubation | 48 h incubation |
| F1 | 0 | 0 |
| F2 | 0 | 0 |
| F3 | 0 | 0 |
| F4 | 0 | 0 |
| BAM 103 | 48 ± 2 | 100 |
| BAM 103 no inoculation | 0 | 0 |
| Stiff Agar | 0* | 0* |

*no penetration inside the gel was detected but penetration at Agar-test tube interface was found to be up to 30 mm The preceding experiment demonstrated the ability of the sol-gel polymer composite formulations to be impermeable to motile bacteria.

Test 2—Evaluation of Sol-Gel Polymer Composite Barrier Properties in an Artificial Glass Cow Teat:

Test 2 was used to evaluate the ability of the sol-gel polymer composite to prevent bacterial migration between two containers. For this experiment, a bottom, first container 1 was filled with nutrient broth and bacteria. A top second container 2 was filled with sterile nutrient broth. The two containers were linked by a simulated glass teat (ø26 mm, 6 cm length, hole ø2.6 mm) filled with the sol-gel polymer composite formulation F3, prepared as described hereinabove. The experiment consisted of tracking the presence or absence of bacterial contamination that may migrate upward into container 2 over time at 37° C.

The bacterial strains presented in Table 12 were selected for the test as a mixed culture that would be representative of a source of bovine mastitis.

TABLE 12

Strain selected for mixed culture in TSB as representative source of bovine mastitis.

| Microorganism | Response | Motility |
|---|---|---|
| Escherichia coli ATCC 25922 | Growth | Positive |
| Staphylococcus aureus ATCC 25923 | Growth | Negative |
| Klebsiella pneumoniae U 3023 | Growth | Negative |

In this experiment, the adhesion between glass and the sol-gel polymer composite plug appeared to be critical for barrier performance. Presence of bubbles, uneven adhesion or successive sol-gel polymer composite transition reduced performance by reducing glass-gel adhesion. This phenomenon was particularly significant at the start of the experiment, provoking a direct merge of the two containers. Tracking glass-gel adhesion failure was performed by addition of Triphenyltetrazolium chloride (TTC 0.5 g/L), a bacteria-sensitive dye, which forms a red precipitate upon reduction in contact with bacteria.

The study of the ability of TTC—labeled F3 to maintain a bacterial barrier property over time was evaluated. On Days 0, 2, 5, 6, 9, 12 and 18, bacterial contamination was evaluated in both sterile and contaminated media compartments. Observations were recorded on Days 0, 3, 6, 14, and 15. Culture medium replacement and fresh inoculation was added to the contaminated compartment on Days 3, 6, 9, and 13. At Day 12, signs of partial adhesion failure began to show a reduction of glass-gel adhesion. On Days 12 and 17, adhesion failure at the glass cow teat interface with the F1-F4 sol-gel polymer composite sample was observed. On Day 15, there was a visual detection of contamination in the upper container 2 above the gel plug (i.e., TTC dye diffusion showed red color in the initially non-contaminated compartment when the well-adhered plug at Day 0 lost adhesion to the glass). At Day 17, the plug stopped to adhere completely to the glass. By Day 18, bacterial contamination quantification by plate count proved sterility breach as the loss of adherence to the glass allowed bacteria to migrate through the gel-glass interface leading to the contamination of container 2.

Knowing the high risk of adhesion breach of sol-gel to glass, this test is thus highly unfavorable to sol-gel performance. Until adhesion failure, the actual performance reported for several tests between 1 and 15 days of experiments and combined in Table 13 shows that F3 prevented bacterial contamination. Petroleum jelly/Paraffin Wax 1:5 control is based on a hydrophobic plug that is known as fully impermeable to bacteria but the control also experienced adhesion issues with glass similar to those observed for the sol-gel composite. Results show the similar performance for this impermeable control and the sol-gel polymer formulations of the disclosure. The performance obtained for F3, between 8 and 15 days during the ability to keep adherence to glass and act as a barrier to bacteria is significantly higher than those observed for the permeable control BAM103 which cannot prevent bacterial contamination after 24 h. Thus, Test 2 provides evidence that the sol-gel composite formulations of the disclosure possessed the ability to be an effective barrier against bacterial migration.

TABLE 13

Summary of barrier properties of different sol-gel and control based on 15 days of incubation experiments.

| Sample | Days before contamination detected up to 15 | Comment |
|---|---|---|
| F1 | 13.5 ± 5 | n = 3. Clear signs of glass-gel adhesion failure prior to contamination. |
| F2 | 8.5 ± 1 | n = 2. Clear signs of glass-gel adhesion failure prior to contamination. |
| F3 | 13 ± 5.5 | n = 3. Clear signs of glass-gel adhesion failure prior to contamination. |
| F4 | 9 | n = 1 |
| BAM 103 | 1 | n = 3 |
| Petroleum Jelly/Paraffin Wax 1:5 | 13 ± 7 | n = 3. Clear signs of glass-Gel adhesion failure prior to contamination. |
| Orbeseal | 15+ | n = 1 |

In summary, Test 1 demonstrated the ability of the sol-gel polymer composite formulations to prevent bacterial migration within 48 hours as compared to a control gel BAM103 that allowed migration of motile bacteria. The results of the different sol-gel polymer composite formulations showed a total impermeability to bacteria, thus preventing bacterial penetration into the gel. In Test 2, the barrier property in the artificial glass cow teat against bacterial migration was shown to last as long as adhesion between glass (simulated substrate) and the sol-gel plug was maintained. Performances were shown to be similar to the impermeable control of paraffin/petroleum jelly and significantly longer than the permeable control of BAM103. Since long-term retention was observed in the in vivo studies described in Examples 7 and 8, it can be appreciated that the sol-gel polymer composite formulations of the disclosure will act as an effective teat sealant barrier against both motile and immotile bacterial migration during the dry period of dairy cows until the sealants are physically removed.

Example 11

Evaluation of Impact of Inorganic Filler on Sol-Gel Rheology

Sol-gel polymer composite formulation F2 (1.5L) was prepared as described above in Example 1 and then mixed with filler (silicon dioxide ($SiO_2$) or nanocrystalline cellulose (NCC)) at various concentrations (1 wt %, 5 wt %, and 20 wt %). The impact of the filler on density and rheological properties of the sol-gel polymer composite formulation was evaluated. Results are shown in Table 14.

TABLE 14

Comparison of the rheological properties of sol-gel polymer composite formulation with and without filler.

| Filler | T (° C.) | G' (Pa) | G" (Pa) | tan δ | Density (g/ml) |
|---|---|---|---|---|---|
| None | 25 | 387.7 | 74.8 | 0.193 | 0.96 |
|  | 37 | 974.5 | 68.4 | 0.071 |  |
| SiO$_2$ 1% | 25 | 194.3 | 66.0 | 0.340 | 1.03 |
|  | 37 | 1067.4 | 65.9 | 0.062 |  |
| SiO$_2$ 5% | 25 | 235.4 | 70.2 | 0.298 | 1.11 |
|  | 37 | 1134.4 | 72.8 | 0.065 |  |
| SiO$_2$ 20% | 25 | 557.7 | 140.9 | 0.253 | 1.09 |
|  | 37 | 2089.0 | 153.6 | 0.074 |  |
| NCC 1% | 25 | 196.4 | 66.2 | 0.337 | 1.08 |
|  | 37 | 1067.8 | 66.6 | 0.063 |  |
| NCC 5% | 25 | 312.0 | 99.8 | 0.320 | 1.08 |
|  | 37 | 1712.5 | 122.7 | 0.072 |  |
| NCC 20% | 25 | — | — | — | 1.18 |
|  | 37 | — | — | — |  |

The results show that the storage modulus (G') increased by increasing the amount of filler in the sol-gel polymer composite formulation, indicating that the higher the solid content in the formulation is, the stiffer the gel would be at 37° C. At 1 and 5 wt. % of SiO$_2$, the loss modulus remained slightly the same compared to the original formulation ("None"). The same observation could be made for the NCC except for the 5 wt % where the G" increased at both temperatures compared to the main material. Concerning the tan δ at 25° C., it increased at 1 wt. % of SiO$_2$ which indicates that gel is flowing better at room temperature compared to the original batch ("None"). It then decreased with the increase of the filler content for the same reasons described previously regarding the solid content. The same behavior was seen for the NCC. No gel transition was clearly observed with 20 wt. % NCC. Finally, the original batch had lower density (0.96 g/ml) than water due to the presence of air bubbles within the sol-gel. The addition of filler up to 20 wt. % to the sol-gel formulation allowed the product to attain a density of about 1.10 g/ml within the error margin of F2 formulation free of air bubbles. In sum, the results show that addition of silicon dioxide inorganic filler allows significant increase of G' (up to about double) for both the sol and gel states without affecting the transition from sol to gel and shear thinning of the formulation.

Example 12

Evaluation of Effect of Chitosan Degree of Deacetylation (DDA) on Sol-Gel Properties Sol-gel polymer composite formulation F2 was prepared as described above in Example 1 using chitosan having varying degrees of deacetylation (% DDA). Results are shown in Table 15.

When the chitosan % DDA in formulation F2 dropped below 76%, the formulation began to lose its sol-gel characteristics. In particular, the tan δ values observed at 25° C. and 37° C., and especially the tan δ ratio (tan δ at 25° C./tan δ at 37° C.), provides an indication and scale of the sol-gel transition. Upon transition to a low % DDA-sourced chitosan (from 90% to 75.5% DDA), a noticeable decrease in F2 performance was observed wherein the tan δ ratio decreased from 3.3-6.4 to 1.2, as shown in Table 15 below.

TABLE 15

Comparative results of % DDA variation between lab-scale and 2 L scale process.

| Scale | % DDA | tanδ at 25° C. | tanδ at 37° C. | tanδ ratio |
|---|---|---|---|---|
| 50 g | 90.0* | 0.275 | 0.043 | 6.4 |
| 1.25 L | 90.0* | 0.227 | 0.047 | 4.8 |
| 1.25 L | 90.0* | 0.253 | 0.076 | 3.3 |
| 50 g | 75.5 | 0.140 | 0.113 | 1.2 |
| 1.25 L | 75.5 | 0.177 | 0.144 | 1.2 |

*% DDA was determined using a different batch of the same specification of reagent-grade chitosan.

In order to explain the decrease in the sol-gel performance, a two-factor Design of Experiment (DOE) was devised. Two parameters of chitosan were considered, namely degree of deacetylation (% DDA) and molecular weight (MW).

The most significant output factors and their expected values for an optimal F2 formulation, while maintaining acceptable tan δ values at 37° C., are the following: Complex viscosity at 25° C.; tan δ at 25° C.; and oscillation stress of gelation.

Complex viscosity shall be low and tan δ at 25° C. values shall be high in order for the F2 formulation to exhibit the most "liquid" character as possible; this would be expected to maximize scale-up processability for the formulation. Oscillation stress of gelation shall be low in order to increase the product's "syringeability", ultimately for repeated product delivery via syringe by the end user. DOE results are summarized in Table 16.

TABLE 16

Summary of results from two-factor design of experiment (DOE).

| Chitosan MW (kDa) | Chitosan % DDA | tanδ at 25° C. | tanδ at 37° C. | tanδ ratio | Complex viscosity (Pa · s) | Oscillation stress (Pa) | Onset of Gelation Temp. (° C.) |
|---|---|---|---|---|---|---|---|
| 84527 | 76.77% | 0.27 | 0.07 | 3.9 | 256 | 218 | 28.8 |
| 55381 | 94.3% | 0.37 | 0.07 | 5.3 | 140 | 150 | 31.0 |
| 467690 | 77.36% | 0.27 | 0.08 | 3.4 | 375 | 217 | 34.0 |
| 404580 | 97.60% | 0.60 | 0.07 | 8.6 | 107 | 119 | 30.1 |

The results shown in Table 16 indicate that % DDA was the most significant factor in decreasing complex viscosity, increasing tan δ at 25° C., and decreasing formulation syringeability. The results of this DOE also suggested that the high MW/high % DDA (404580 kDa, 97.6% DDA) chitosan produced an optimal formulation in terms of these properties. The resulting formulation yielded the least viscous (complex viscosity), most viscous liquid—as opposed to gel-like—nature (tan δ at 25° C.) and the most syringeable formulation (oscillation stress) of all samples examined whilst maintaining a suitably viscous gel at 37° C. (tan δ at 37° C.). The results suggest that, in some embodiments, chitosan having a % DDA of about 77% or higher is required to obtain functional sol-gel.

Example 13

Preparation and Properties of Sol-Gel Polymer Composites

A polymer composite formulation was prepared as follows below. Table A shows the formulation. The formulation was prepared in a batch of about 220 grams.

TABLE A

|  | | Amount (w %) |
|---|---|---|
| ELASTOSIL ® RT 625A | | 50.7% |
| F3V2 | Methylcellulose | 4.9% |
|  | Chitosan | 1.0% |
|  | Acetic Acid | 0.5% |
|  | Potassium phosphate dibasic | 0.2% |
|  | β-glycerophosphate disodium salt hydrate | 0.07% |
|  | Water D.I. | 42.7% |

Deionized water and chitosan ChitoClear were mixed with glacial acetic acid until a homogenous mixture was achieved. Methylcellulose A15 Premium (from Dow) was added to such mixture at room temperature until a homogenous mixture was achieved. Thereafter, a salt solution of potassium phosphate dibasic and β-glycerophosphate disodium salt hydrate were added to such mixture at room temperature until a homogeneous mixture was achieved, thereby forming a chitosan composition (F3V2).

ELASTOSIL® RT 625A was added to the chitosan composition at room temperature and then heated at 60° C. for at least 10 minutes until a homogenous mixture was obtained. The final composition consisted of about 50% ELASTOSIL® RT 625A and about 50% chitosan composition.

The composition formed had an appearance at 25° C. of a beige viscous liquid. The solid content was about 57.3% and the pH was about 5.3.

Initial in vivo testing demonstrated that F3v2+PDMS (shown above in Table A) had significant material recovered from 12 of 16 quarters (75%), while the positive control had significant material found in 15 of 16 quarters (93.8%).

The sample was steam sterilized by autoclaving and testing was performed to determine various physical characteristics. This material maintained thermal gelling properties, with the gel point occurring at about 33-35° C. The storage modulus of the material at room temperature (20° C.) is 900-1200 Pa, while at physiological temperature (37° C.) increased to 3000-8000 Pa.

Syringe Force

The force required to expel the majority of the material from a syringe with a standard intramammary cannula (~1.3-1.5 mm ID) in about one second was measured using a TA.XT plus Texture Analyzer. The average of the maximum force achieved during administration for F3v2+PDMS was 130-150N.

Specific Gravity

The specific gravity of the material is measured by volume displacement. A 5 mL graduated cylinder was filled with 3 mL (a) of water, and the weight was recorded (c). Material was added until the volume was at 5 mL (b), and the weight was recorded (d). The specific gravity was determined by the following equation:

$$\rho = \frac{d-b}{c-a}$$

The F3v2+PDMS formulation has an average specific gravity of 1.03-1.10 g/mL.

Viscosity

For this testing, using Anton-Paar Rheometer and CP25-2, the maximum initial viscosity and average sheared viscosity was determined by increasing the shear rate, measuring shear stress, and calculating viscosity at 20° C. The maximum initial viscosity was 1100-1400 Pa-s, while the average sheared viscosity was 20-25 Pa-s.

Structure Recovery

Structure recovery represents the ability of the product to return to its original condition following a high shear condition, such as administration through an intramammary cannula. For this testing, using Anton-Paar Rheometer and PP25, the material was measured at rest, followed by a brief shear event, representing the administration. The material was allowed to recover for ten minutes at physiological temperatures and percent recovery was determined by the differences. The F3v2+PDMS sample had greater than 100% structure recovery.

F3v2+PDMS: Ratios and Compositions

Below are formulation work and testing of various ratios of F3+PDMS or F3v2+PDMS.

Comparison of F3 and F3v2 compositions used in testing:

TABLE B

| Components | F3 (wt. %) | F3v2 (wt. %) |
|---|---|---|
| Methyl Cellulose | 8 | 9.7 |
| Chitosan | 2 | 2 |
| Potassium phosphate dibasic trihydrate | 0.36 | 0.3 |
| Sodium pyrophosphate tetrabasic (F3) or Sodium Beta Glycerophosphate (F3v2) | 0.03 | 0.13 |
| Water for salt solution | 9.62 | 4.77 |
| Acetic acid | 0.48 | 1 |
| Water for acetic acid | 79.52 | 82.1 |

Testing with F3 and Wacker Elastosil® RT 625A was performed using 30-60% Wacker Elastosil® RT 625A, and results are shown in the table below:

TABLE C

| F3 (wt. %) | Wacker Elastosil ® RT 625A (wt. %) | Relative Density | 24 hour Stability |
|---|---|---|---|
| 40 | 60 | Sinks | No change |
| 50 | 50 | Sinks | No change |
| 60 | 40 | Sinks | No change |
| 70 | 30 | Sinks | No change |

Testing with F3v2 and Wacker Elastosil® RT 625A was performed using 25-50% Wacker Elastosil® RT 625A, and results are shown in the table below.

TABLE D

| F3v2 (wt. %) | Wacker Elastosil ® RT 625A (wt. %) | Relative Density | 24 hour Stability |
|---|---|---|---|
| 50 | 50 | Sinks | No Change |
| 75 | 25 | Floats | Degrades |

Testing with F3v2 and food-grade alternatives to Wacker Elastosil® RT 625A was performed using Elastosil® M4600 and Elastosil® M4601, and results are shown in the table below.

TABLE E

| F3v2 (wt. %) | Wacker Elastosil ® (wt. %) | Relative Density | 24 hour Stability |
|---|---|---|---|
| 25 | 75 - M4600 | Sinks | No Change |
| 40 | 60 - M4601 | Sinks | No Change |

Each test formulation prepared above was subjected to a stress sweep test to determine both the storage and loss moduli as a function of stress at fixed frequency. At low applied stresses, the values of storage modulus (G') were constant and covered a broad spectrum, ranging from 354 to 20,000 Pa. Shear thinning behavior, measured by decrease of storage modulus (G') as a function of the applied stress, was observed at higher stress values. Shear-thinning region also covered a broad range starts at 2-100 Pa, depending on composition. The controlled shear method for determination of viscosity provided maximum initial viscosity ranges from 400-1400 Pa-s, while the average sheared viscosity was 10-25 Pa-s for the test formulations.

Additional physical property data was collected on the test formulations as follows:

TABLE F

| F3:RT625A | pH | G' at 20° C. (pre-shear) | G' at 37° C. (post-shear) | Percent Recovery |
|---|---|---|---|---|
| 40:60 | 4.9 | 929 Pa | 1482 Pa | 160% |
| 50:50 | 5.0 | 20840 Pa | 20000 Pa | 96% |
| 60:40 | 6.1 | 817 Pa | 2027 Pa | 250% |
| 70:30 | 6.2 | 354 Pa | 641 Pa | 180% |
| 100:0 | 6.3 | 200 Pa | 175 Pa | 87.5% |

TABLE G

| F3v2:RT625A | pH | Ease of Administration | Viscosity |
|---|---|---|---|
| 50:50 | 4.6 | Moderately Difficult | 280 Pa-s |
| 75:25 | 5.0 | Moderate | 62 Pa-s |

TABLE H

| F3v2:M4600 or M4601 | pH | Ease of Administration |
|---|---|---|
| 25:75 | 4.0 | Moderate |
| 40:60 | 4.0 | Difficult |

In the foregoing, there has been provided a detailed description of particular embodiments of the present disclosure for the purpose of illustration and not limitation. It is to be understood that all other modifications, ramifications and equivalents obvious to those having skill in the art based on this disclosure are intended to be included within the scope of the disclosure as claimed.

What is claimed is:

1. A product for preventing or treating a mammary disorder in a female non-human animal, the product comprising an effective amount of a sol-gel polymer composite comprising chitosan, a hydrophilic polymer separate from chitosan, a gelation agent, a suitable medium, and a polysiloxane;
   wherein the polysiloxane is present in an amount of about 30-70% by weight;
   wherein the sol-gel polymer composite is configured to undergo a liquid-solid phase transition in response to one or more physiological stimuli arising from contact of the sol-gel polymer composition with a mammalian subject to form the product as a strong solid being evidenced by having an elastic modulus (G') of about 450 Pa to about 10,000 Pa;
   wherein the one or more physiological stimuli is selected from the group consisting of breast milk, udder secretions, or combinations thereof;
   wherein the liquid-solid phase transition is reversible; and
   wherein the gelation agent is configured to undergo physical crosslinking in response to the one or more stimuli.

2. The product according to claim 1, wherein the medium is aqueous acetic acid.

3. The product according to claim 1, wherein the chitosan is acylated.

4. The product according to claim 1, wherein the polysiloxane is dimethylpolysiloxane (PDMS).

5. The product according to claim 1, wherein the hydrophilic polymer is a water-soluble polysaccharide.

6. The product according to claim 5, wherein the water-soluble polysaccharide is cellulose or a derivative thereof.

7. The product according to claim 1, wherein the hydrophilic polymer is selected from the group consisting of methylcellulose, polyvinyl acetate, polyvinyl acetate-acylate, hydroxypropylcellulose, hydroxypropyl methylcellulose, ethyl hydroxylethyl cellulose, hypromellose acetate succinate, hyaluronic acid, nomomc triblock copolymer, polyethyleneglycol, sodium alginate and gelatin.

8. The product according to claim 1, wherein the gelation agent is a salt selected from the group consisting of -Glycerophosphate disodium hydrate, -Glycerophosphate disodium pentahydrate, sodium pyrophosphate tetrabasic, potassium phosphate dibasic trihydrate, sodium hexametaphosphate, sodium tetrapolyphosphate, sodium hexapolyphosphate, sodium heptapolyphosphate, sodium octapolyphosphate, sodium tripolyphosphate and sodium polyphosphate, potassium ferricyanide and a mixture thereof.

9. The product according to claim 1, wherein the gelation agent is an ionic crosslinking agent selected from the group consisting of lipophilic phosphates, plasticizers, anionic surfactants, gums, pectin, carrageenan (iota, kappa, and lambda), alginate, cyclodextrins, and a mixture thereof.

10. The product according to claim 1, wherein the sol-gel polymer composite further comprises one or more antimicrobial agents.

11. The product according to claim 10, wherein the antimicrobial agent is selected from the group consisting of a macrolide, a cephalosporin, a lincosaminide antibiotic, a fluoroquinolone, a tetracycline, a penicillin, a spectinomycin, a sulfonamide, a chloramphenicol, a fluorinated synthetic analog of thiamphenicol and a mixture thereof.

12. The product according to claim 11, wherein the antimicrobial agent is a cephalosporin and the cephalosporin is ceftiofur hydrochloride.

13. A method of preventing or treating a mammary disorder in a female non-human animal, comprising administering an effective amount of the sol-gel polymer composite of any of claims 1-9 and 10-12 to a teat, a teat canal or a teat cistern of the animal.

14. A system for forming a physical barrier in the teat canal or cistern of a non-human animal for the prevention or treatment of a mammary disorder wherein the system comprises a delivery device containing the sol-gel polymer composite of any of claims 1-9 and 10-12.

15. A product for preventing or treating a mammary disorder in a female non-human animal, the product comprising an emulsion formed of:

about 55% to about 90% by volume (based on the total volume of the product) of a sol-gel polymer composite comprising chitosan, a hydrophilic polymer separate from chitosan, a gelation agent, a suitable medium, and a polysiloxane;

wherein the polysiloxane is present in an amount of about 30-70% by weight; and about 10% to about 45% by weight (based on the total weight of the product) of an oil;

wherein the sol-gel polymer composite is configured to undergo a liquid-solid phase transition in response to one or more physiological stimuli, wherein the one or more physiological stimuli is selected from the group consisting of breast milk, udder secretions, or combinations thereof;

wherein the liquid-solid phase transition is reversible; and wherein the gelation agent is configured to undergo physical crosslinking in response to the one or more stimuli.

* * * * *